(12) United States Patent
Shimazu et al.

(10) Patent No.: US 11,123,278 B2
(45) Date of Patent: Sep. 21, 2021

(54) HAIR COSMETIC

(71) Applicant: KAO CORPORATION, Tokyo (JP)

(72) Inventors: Ayako Shimazu, Arakawa-ku (JP); Yoichi Saito, Kita-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/765,038

(22) PCT Filed: Nov. 19, 2018

(86) PCT No.: PCT/JP2018/042712
§ 371 (c)(1),
(2) Date: May 18, 2020

(87) PCT Pub. No.: WO2019/098374
PCT Pub. Date: May 23, 2019

(65) Prior Publication Data
US 2020/0360255 A1 Nov. 19, 2020

(30) Foreign Application Priority Data

Nov. 20, 2017 (JP) .............................. JP2017-223225
Apr. 13, 2018 (JP) .............................. JP2018-078015

(51) Int. Cl.
A61Q 5/10 (2006.01)
A61K 8/49 (2006.01)
A61K 8/34 (2006.01)
A61K 8/41 (2006.01)
A61K 8/86 (2006.01)

(52) U.S. Cl.
CPC .............. *A61K 8/492* (2013.01); *A61K 8/342* (2013.01); *A61K 8/416* (2013.01); *A61K 8/86* (2013.01); *A61Q 5/10* (2013.01)

(58) Field of Classification Search
CPC . A61Q 5/10; A61Q 5/065; A61K 8/49; A61K 8/342; A61K 8/86; A61K 8/39; A61K 8/416; A61K 8/492; A61K 2800/5426
USPC .......................................................... 8/405
See application file for complete search history.

(56) References Cited

U.S. PATENT DOCUMENTS

| | | | |
|---|---|---|---|
| 2003/0051297 A1 | 3/2003 | Patel et al. | |
| 2003/0074748 A1 | 4/2003 | Patel et al. | |
| 2004/0255398 A1 | 12/2004 | Saito et al. | |
| 2010/0037404 A1* | 2/2010 | Koike | A61K 8/891 8/423 |
| 2010/0125956 A1* | 5/2010 | Koike | A61Q 5/10 8/429 |
| 2010/0154135 A1* | 6/2010 | Matsunaga | A61K 8/817 8/406 |
| 2010/0170048 A1* | 7/2010 | Koike | A61K 8/492 8/407 |

FOREIGN PATENT DOCUMENTS

| | | |
|---|---|---|
| JP | 2001-10938 A | 1/2001 |
| JP | 2002-53436 A | 2/2002 |
| JP | 2003-55175 A | 2/2003 |
| JP | 2003-146857 A | 5/2003 |
| JP | 2004-525130 A | 8/2004 |
| JP | 2009-137877 A | 6/2009 |
| JP | 2014-24766 A | 2/2014 |

(Continued)

OTHER PUBLICATIONS

STIC Search Report dated Dec. 29, 2020.*
International Search Report dated Feb. 26, 2019 in PCT/JP2018/042712 filed on Nov. 19, 2018, 2 pages.
U.S. Appl. No. 16/765,061, filed May 18, 2020, Sakai, Yuta et al.
U.S. Appl. No. 16/765,033, filed May 18, 2020, Yoshida, Hiroshi et al.

(Continued)

*Primary Examiner* — Eisa B Elhilo
(74) *Attorney, Agent, or Firm* — Oblon, McClelland, Maier & Neustadt, L.L.P.

(57) ABSTRACT

The present invention relates to a hair cosmetic containing the following components (A) to (C):

(A) a compound represented by the following general formula (1) or a salt thereof:

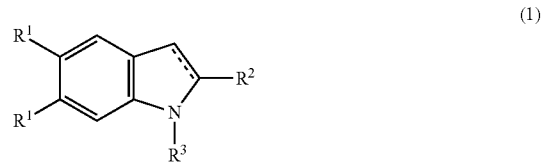

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a cationic surfactant; and (C) a polyoxyethylene addition type nonionic surfactant, wherein a mass ratio of the component (B) to the component (A) [(B)/(A)] is 1.0 or more; a mass ratio of the component (C) to the component (A) [(C)/(A)] is 1.0 or more; a mass ratio of t a component having an oxyethylene addition molar number of 5 or more in the components constituting the component (C) to the component (A) is satisfied with a predetermined requirement; and a pH at 25° C. of the hair cosmetic is 8.0 or more and 12.0 or less.

14 Claims, No Drawings

(56) References Cited

FOREIGN PATENT DOCUMENTS

WO    WO 2008/149535 A1    12/2008

OTHER PUBLICATIONS

U.S. Appl. No. 16/765,046, filed May 18, 2020, Nagayama, Ayami.
U.S. Appl. No. 16/765,067, filed May 18, 2020, Shimazu, Ayako et al.
Extended European Search Report dated Jul. 26, 2021, in European patent application No. 18877677.7, 7 pages.

* cited by examiner

HAIR COSMETIC

FIELD OF THE INVENTION

The present invention relates to a hair cosmetic.

BACKGROUND OF THE INVENTION

Conventionally, as a hair dye for gray hair dyeing, an air-oxidative hair dye using 5,6-dihydroxyindole, 5,6-dihydroxyindoline, or a derivative thereof, each of which is a melanin precursor, is known. Such a melanin precursor does not use an oxidizing agent, and therefore, even in the case of being used for a hair dye, it is less in damage of the hair, and it is high in convenience as a dye for hair dye.

For example, PTL 1 discloses a one-part air-oxidative hair dye containing the aforementioned melanin precursor and having excellent dyeing properties.

CITATION LIST

Patent Literature

PTL 1: JP 2003-146857 A

SUMMARY OF THE INVENTION

The present invention relates to the following.
A hair cosmetic containing the following components (A) to (C):

(A) a compound represented by the following general formula (1) or a salt thereof:

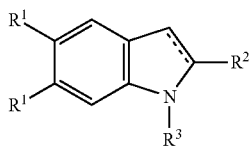

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a cationic surfactant; and (C) a polyoxyethylene addition type nonionic surfactant, wherein a mass ratio of the component (B) to the component (A) [(B)/(A)] is 1.0 or more, and a mass ratio of the component (C) to the component (A) [(C)/(A)] is 1.0 or more; when in components constituting the component (C), a component having an oxyethylene addition molar number of 5 or more is designated as (C), a component having an oxyethylene addition molar number of 10 or more is designated as ($C_{10}$), a component having an oxyethylene addition molar number of 15 or more is designated as ($C_{15}$), and a component having an oxyethylene addition molar number of 30 or more is designated as ($C_{30}$), a mass ratio of each of the components relative to the component (A) is satisfied with at least one of the following expressions (I) to (IV); and a pH at 25° C. of the hair cosmetic is 8.0 or more and 12.0 or less:

$(C_5)/(A) \geq 4.5$      (I)

$(C_{10})/(A) \geq 3.5$      (II)

$(C_{15})/(A) \geq 1.2$      (III)

$(C_{30})/(A) \geq 0.2$      (IV)

DETAILED DESCRIPTION OF THE INVENTION

[Hair Cosmetic]

The hair cosmetic of the present invention is a hair cosmetic containing the following components (A) to (C):

(A) a compound represented by the following general formula (1) or a salt thereof:

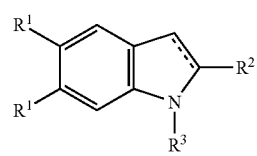

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a cationic surfactant; and (C) a polyoxyethylene addition type nonionic surfactant, wherein a mass ratio of the component (B) to the component (A) [(B)/(A)] is 1.0 or more, and a mass ratio of the component (C) to the component (A) [(C)/(A)] is 1.0 or more; when in components constituting the component (C), a component having an oxyethylene addition molar number of 5 or more is designated as (C), a component having an oxyethylene addition molar number of 10 or more is designated as ($C_{10}$), a component having an oxyethylene addition molar number of 15 or more is designated as ($C_{15}$), and a component having an oxyethylene addition molar number of 30 or more is designated as ($C_{30}$), a mass ratio of each of the components relative to the component (A) is satisfied with at least one of the following expressions (I) to (IV); and a pH at 25° C. of the hair cosmetic is 8.0 or more and 12.0 or less:

$(C_5)/(A) \geq 4.5$      (I)

$(C_{10})/(A) \geq 3.5$      (II)

$(C_{15})/(A) \geq 1.2$      (III)

$(C_{30})/(A) \geq 0.2$      (IV)

The hair cosmetic of the present invention contains both the component (A) that is a melanin precursor and the component (B) that is a cationic surfactant, and even in an alkaline region, it hardly produces an aggregate to be caused owing to complex formation of these components and has favorable stability.

The present inventors have found that only in the case where among nonionic surfactants, the component (C) that is a polyoxyethylene addition type nonionic surfactant is regulated such that its content is 1.0 or more in terms of a mass ratio relative to the component (A) and used so as to have an addition molar number of oxyethylene of 5 or more in a specified mass ratio relative to the component (A), the production of the aforementioned aggregate can be suppressed.

In addition, the present inventors have found that by regulating the mass ratio (B)/(A) of the component (B) to the component (A) in the hair cosmetic to 1.0 or more, even in an alkaline region, a polymerization reaction of the component (A) outside the hair is suppressed, so that not only the touch during rinsing is improved, but also the hair dyeing properties are improved.

Although the technique disclosed in PTL 1 is a technique regarding the hair dye, during use of a hair dye, a lot of time and energy are spent, such that a care for preventing staining of a place where hair dyeing is carried out, such as a bathroom and a lavatory, is needed, so that it may not be said that the foregoing technique is a daily simply usable, and a long period of time is required in order to obtain a hair dyeing effect to some extent. Then, the present inventors thought that by blending the aforementioned melanin precursor in a hair cosmetic capable of being daily used in a bathroom, high hair dyeing properties can be exhibited simply and for a short period of time, and made investigations.

Meanwhile, when air oxidation of the aforementioned melanin precursor rapidly proceeds, a polymerization reaction occurs outside the hair, and a polymerized pigment is adsorbed on the hair surface, and therefore, the touch of the hair after hair dyeing is occasionally lowered.

In a so-called in-bath hair care product to be used in a bathroom, it is known to use a cationic substance, such as a cationic surfactant, in order to make the touch of the hair during applying on the hair or after drying favorable and to reduce damage of the hair. Then, the present inventors have found that when a cationic surfactant is blended in a hair cosmetic using a melanin precursor, surprisingly, the polymerization reaction outside the hair is suppressed, and the touch during rinsing is improved. However, it has become clear that since 5,6-dihydroxyindole, 5,6-dihydroxyindoline, or a derivative thereof, each of which is a melanin precursor, manifests anionic properties in an alkaline region, it forms a complex together with the cationic surfactant, to produce an aggregate. When the aggregate is produced, not only stability or appearance of the product is impaired, but also it becomes difficult to penetrate sufficient amounts of the active ingredients into the hair.

A problem of the present invention is to provide a hair cosmetic which contains a predetermined melanin precursor and a cationic surfactant, hardly produces an aggregate and has excellent stability even in an alkaline region, and is able to make the touch of the hair after the treatment favorable.

The present inventors have found that the aforementioned problem can be solved by a hair cosmetic containing a predetermined melanin derivative, a cationic surfactant, a predetermined nonionic surfactant in specified ratios.

The hair cosmetic of the present invention hardly produces an aggregate to be caused owing to complex formation between a predetermined melanin precursor and a cationic surfactant even in an alkaline region and is excellent in stability and favorable in touch of the hair during rinsing.

In the present invention, examples of the hair cosmetic include a hair cleansing agent, such as a shampoo, a hair rinse, a hair conditioning agent, a hair treatment agent, a hair styling agent, a hair growth promoter, and a hair dye. Of these, a hair cosmetic selected from the group consisting of a hair rinse, a hair conditioning agent, and a hair treatment agent is preferred.

The formulation of the composition is not particularly limited, and it is possible to take an arbitrary formulation, for example, a liquid, a foam, a paste, a cream, a solid, and a powder. From the viewpoint of applicability on the hair, the formulation is preferably a liquid, a paste, or a cream.

<Component (A)>

The hair cosmetic of the present invention contains the component (A) that is a compound represented by the following general formula (1) or a salt thereof. The component (A) is a melanin precursor which is polymerized through air oxidation and converted to a melanin pigment and acts as a dyeing agent of hair.

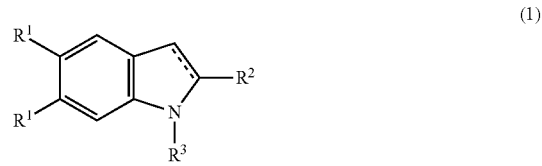

(1)

In the formula, a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group.

The melanin precursor of the component (A) is an indole derivative or an indoline derivative that is the compound represented by the general formula (1), or a salt thereof, and in the present invention, one or a combination of two or more thereof can be used. From the viewpoint of hair dyeing properties, the component (A) is more preferably an indole derivative (namely, a π bond exists in the broken line portion in the general formula (1)).

From the viewpoint of availability and hair dyeing properties of the component (A), in the general formula (1), $R^1$ is preferably a hydroxy group; $R^2$ is preferably a hydrogen atom or —COOR (R is a hydrogen atom, a methyl group, or an ethyl group), and more preferably a hydrogen atom or —COOH; and $R^3$ is preferably a hydrogen atom.

Examples of the compound represented by the general formula (1) include 5,6-dihydroxyindole, 5,6-dihydroxyindole-2-carboxylic acid, methyl 5,6-dihydroxyindole-2-carboxylate, ethyl 5,6-dihydroxyindole-2-carboxylate, N-methyl-5,6-dihydroxyindole, N-methyl-5,6-dihydroxyindole-2-carboxylic acid, N-ethyl-5,6-dihydroxyindole, N-ethyl-5,6-dihydroxyindole-2-carboxylic acid, N-acetyl-5,6-dihydroxyindole, N-acetyl-5,6-dihydroxyindole-2-carboxylic acid, 5-acetoxy-6-hydroxyindole, 5-acetoxy-6-hydroxyindole-2-carboxylic acid, 5,6-dihydroxyindoline, 5,6-dihydroxyindoline-2-carboxylic acid, methyl 5,6-dihydroxyindoline-2-carboxylate, ethyl 5,6-dihydroxyindoline-2-carboxylate, N-methyl-5,6-dihydroxyindoline, N-methyl-5,6-dihydroxyindoline-2-carboxylic acid, N-ethyl-5,6-dihydroxyindoline, N-ethyl-5,6-dihydroxyindoline-2-carboxylic acid, N-acetyl-5,6-dihydroxyindoline, N-acetyl-5,6-dihydroxyindoline-2-carboxylic acid, 5-acetoxy-6-hydroxyindoline, and 5-acetoxy-6-hydroxyindoline-2-carboxylic acid.

Examples of the salt of the compound represented by the general formula (1) include a hydrochloride, a hydrobromide, a sulfate, a phosphate, an acetate, a propionate, a lactate, and a citrate of the foregoing compounds. Above all, a hydrobromide is preferred from the viewpoint of availability.

In the general formula (1), when $R^2$ is —COOH, examples of the salt of the compound represented by the general formula (1) include carboxylates thereof ($R^2$ is —COO$^-$X$^+$ (X$^+$ is a cation, such as an alkali metal ion, e.g., Na$^+$ and K$^+$, an alkaline earth metal ion, e.g., Ca$^+$ and Mg$^+$, and an ammonium ion)).

From the viewpoint of dyeing the hair in a natural color shade, the component (A) is preferably one or more selected from the group consisting of 5,6-dihydroxyindole, 5,6-dihydroxyindole-2-carboxylic acid, 5,6-dihydroxyindoline, and 5,6-dihydroxyindoline-2-carboxylic acid, and salts thereof; more preferably one or more selected from the group consisting of 5,6-dihydroxyindole, 5,6-dihydroxyindole-2-carboxylic acid, and 5,6-dihydroxyindoline hydrobromide; still more preferably one or two selected from the group consisting of 5,6-dihydroxyindole and 5,6-dihydroxyindole-2-carboxylic acid; and yet still more preferably a combination of 5,6-dihydroxyindole and 5,6-dihydroxyindole-2-carboxylic acid.

In the case of use of a combination of 5,6-dihydroxyindole and 5,6-dihydroxyindole-2-carboxylic acid, a molar ratio thereof is preferably in a range of 50/50 to 99/1, more preferably in a range of 80/20 to 99/1, and still more preferably in a range of 85/15 to 95/5. When the molar ratio of 5,6-dihydroxyindole and 5,6-dihydroxyindole-2-carboxylic acid falls within the aforementioned range, finish of the hair after hair dyeing becomes close to a natural color tint.

The molar ratio of 5,6-dihydroxyindole and 5,6-dihydroxyindole-2-carboxylic acid can be quantitatively determined by means of reversed phase HPLC.

From the viewpoint of improvement in hair dyeing properties, the content of the component (A) in the hair cosmetic is preferably 0.05% by mass or more, and more preferably 0.07% by mass or more, and from the viewpoint of touch during rinsing of hair and the viewpoint of economy, it is preferably 5% by mass or less, more preferably 2% by mass or less, still more preferably 1% by mass or less, yet still more preferably 0.8% by mass or less, and even yet still more preferably 0.5% by mass or less.

<Component (B)>

The hair cosmetic of the present invention contains a cationic surfactant as the component (B). The component (B) has an action of not only suppressing a polymerization reaction of the component (A) outside the hair to improve the hair dyeing properties but also making the touch during rinsing of hair after the treatment with the hair cosmetic favorable.

Examples of the cationic surfactant include a mono- or di-long chain alkyl quaternary ammonium salt represented by the following general formula.

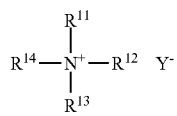

In the formula, $R^{11}$ represents a linear or branched alkyl group having 8 or more and 22 or less carbon atoms, or a group represented by $R^{15}CONH(CH_2)_m$—, $R^{15}$—O—$(CH_2)_m$—, or $R^{15}COO(CH_2)_m$— ($R^{15}$ represents a linear or branched alkyl group having 7 or more and 21 or less carbon atoms, and m represents a number of 1 or more and 4 or less); $R^{12}$ represents a linear or branched alkyl group having 1 or more and 22 or less carbon atoms, or a group represented by the foregoing $R^{15}CONH(CH_2)_m$—, $R^{15}$—O—$(CH_2)_m$—, or $R^{15}COO(CH_2)_m$—; $R^{13}$ and $R^{14}$ each independently represent an alkyl group having 1 or more and 4 or less carbon atoms; and Y$^-$ represents a chloride ion, a bromide ion, or a methosulfate ion.

In the aforementioned general formula, preferably, $R^{11}$ represents a linear or branched alkyl group having 8 or more and 22 or less carbon atoms, or a group represented by $R^{15}$—O—$(CH_2)_m$— ($R^{15}$ represents a linear or branched alkyl group having 7 or more and 21 or less carbon atoms, and m represents a number of 1 or more and 4 or less); $R^{12}$ represents a linear or branched alkyl group having 1 or more and 22 or less carbon atoms, or a group represented by the aforementioned $R^{15}$—O—$(CH_2)_m$—; $R^{13}$ and $R^{14}$ each independently represent an alkyl group having 1 or more and 4 or less carbon atoms; and Y$^-$ represents a chloride ion.

The carbon number of the linear or branched alkyl group in $R^{11}$ is 8 or more and 22 or less, and preferably 8 or more and 18 or less.

The carbon number of the linear or branched alkyl group having 1 or more and 22 or less carbon atoms in $R^{12}$ is preferably 1 or more and 4 or less, and more preferably 1 or more and 3 or less in the case of a mono-long chain alkyl quaternary ammonium salt; and it is preferably 8 or more and 22 or less, and more preferably 8 or more and 18 or less in the case of a di-long chain alkyl quaternary ammonium salt.

$R^{13}$ and $R^{14}$ are each independently a hydrogen atom or an alkyl group having 1 or more and 4 or less carbon atoms, and preferably a methyl group.

The carbon number of the linear or branched alkyl group in $R^{15}$ is 7 or more and 21 or less, and preferably 7 or more and 19 or less.

As specific examples of the cationic surfactant, from the viewpoint of imparting an excellent touch to the hair, one or more selected from the group consisting of a monoalkyltrimethylammonium chloride, a dialkyldimethylammonium chloride, a monoalkyloxyalkyltrimethylammonium chloride, and a monoalkyltrimethylammonium bromide are preferred; and one or more selected from the group consisting of a monoalkyltrimethylammonium chloride and a monoalkyloxyalkyltrimethylammonium chloride are preferred. Above all, one or more selected from the group consisting of behenyltrimethylammonium chloride, stearyltrimethylammonium chloride (steartrimonium chloride), cetyltrimethylammonium chloride (cetrimonium chloride), lauryltrimethylammonium chloride (laurytrimonium chloride), a dialkyl($C_{12}$-$C_{18}$)dimethylammonium chloride, and octadecyloxypropyltrimethylammonium chloride are more preferred. From the viewpoint of imparting an excellent touch to the hair and the viewpoint of suppressing the production of an aggregate, one or more selected from the group consisting of stearyltrimethylammonium chloride, cetyltrimethylammonium chloride, lauryltrimethylammonium chloride, a dialkyl($C_{12}$-$C_{18}$)dimethylammonium chloride, and octadecyloxypropyltrimethylammonium chloride are still more preferred.

From the viewpoint of improvement in touch of the hair, the content of the component (B) in the hair cosmetic may be 1.0 or more in terms of a mass ratio of the component (B) to the component (A) [(B)/(A)], and from the viewpoint of improvement in touch of the hair, it is preferably 1.2 or more, more preferably 1.5 or more, and still more preferably 2.0 or more. In addition, from the viewpoint of suppressing a lowering of touch of the hair, the content of the component (B) in the hair cosmetic is preferably 20 or less, more preferably 15 or less, and still more preferably 12 or less.

However, from the viewpoint of improvement in touch during rinsing of hair and improvement in hair dyeing properties, the content of the component (B) in the hair cosmetic is preferably 0.05% by mass or more, more preferably 0.1% by mass or more, still more preferably 0.2% by mass or more, yet still more preferably 0.3% by mass or more, even yet still more preferably 0.4% by mass or more, and even still more preferably 0.5% by mass or more. In addition, from the viewpoint of suppressing a lowering of touch of the hair, the content of the component (B) in the hair cosmetic is preferably 10% by mass or less, more preferably 5% by mass or less, still more preferably 3% by mass or less, yet still more preferably 2% by mass or less, and even yet still more preferably 1.5% by mass or less.

<Component (C)>

The hair cosmetic of the present invention contains a polyoxyethylene addition type nonionic surfactant as the component (C).

Specifically, examples of the polyoxyethylene addition type nonionic surfactant include a polyoxyethylene alkyl ether, a polyoxyethylene alkenyl ether, a polyoxyethylene mono-fatty acid ester, and a polyoxyethylene sorbitan fatty acid ester. These alkyl group and alkenyl group may be either linear or branched. In addition, the aliphatic chain in the fatty acid may be either saturated or unsaturated and may be either linear or branched.

From the viewpoint of suppressing the production of an aggregate, the carbon number of each of the aforementioned alkyl group, alkenyl group, and aliphatic chain in the fatty acid is preferably 8 or more, more preferably 10 or more, and still more preferably 12 or more, and it is preferably 22 or less, more preferably 20 or less, and still more preferably 18 or less.

Examples of the polyoxyethylene alkyl ether include polyoxyethylene lauryl ether, polyoxyethylene myristyl ether, polyoxyethylene cetyl ether, polyoxyethylene stearylether, and polyoxyethylene behenylether.

Examples of the polyoxyethylene alkenyl ether include polyoxyethylene tetradecenyl ether, polyoxyethylene hexadecenyl ether, and polyoxyethylene octadecenyl ether.

Examples of the polyoxyethylene mono-fatty acid ester include polyoxyethylene monolaurate, polyoxyethylene monomyristate, polyoxyethylene monopalmitate, and polyoxyethylene monostearate.

Examples of the polyoxyethylene sorbitan fatty acid ester include polyoxyethylene sorbitan monolaurate, polyoxyethylene sorbitan monopalmitate, polyoxyethylene sorbitan monostearate, polyoxyethylene sorbitan monooleate, polyoxyethylene sorbitan monoisostearate, polyoxyethylene sorbitan distearate, and polyoxyethylene sorbitan tristearate.

The component (C) can be used alone or in combination of two or more thereof. Above all, the component (C) is preferably one or more selected from the group consisting of a polyoxyethylene alkyl ether, a polyoxyethylene alkenyl ether, and a polyoxyethylene mono-fatty acid ester; more preferably a polyoxyethylene alkyl ether; still more preferably one or more selected from the group consisting of polyoxyethylene lauryl ether, polyoxyethylene myristyl ether, polyoxyethylene cetyl ether, polyoxyethylene stearyl ether, and polyoxyethylene behenyl ether; and yet still more preferably polyoxyethylene cetyl ether.

From the viewpoint of suppressing the production of an aggregate, the content of the component (C) in the hair cosmetic may be 1.0 or more in terms of a mass ratio of the component (C) to the component (A) [(C)/(A)]. From the viewpoint of suppressing the production of an aggregate, the foregoing mass ratio is preferably 1.5 or more, more preferably 2.0 or more, and still more preferably 2.5 or more. In addition, from the viewpoint of suppressing a lowering of touch of the hair, the foregoing mass ratio is preferably 40 or less, more preferably 30 or less, still more preferably 25 or less, yet still more preferably 20 or less, and even yet still more preferably 15 or less.

From the viewpoint of suppressing the production of an aggregate, the component (C) of the hair cosmetic of the present invention is one having an oxyethylene addition molar number of preferably 5 or more, more preferably 10 or more, still more preferably 15 or more, and yet still more preferably 20 or more, and preferably 200 or less, more preferably 180 or less, still more preferably 150 or less, yet still more preferably 100 or less, and even yet still more preferably 70 or less.

In the hair cosmetic of the present invention, when in components constituting the component (C), a component having an oxyethylene addition molar number of 5 or more is designated as ($C_5$), a component having an oxyethylene addition molar number of 10 or more is designated as ($C_{10}$), a component having an oxyethylene addition molar number of 15 or more is designated as ($C_{15}$), and a component having an oxyethylene addition molar number of 30 or more is designated as ($C_{oo}$), a mass ratio of each of the components relative to the component (A) is satisfied with at least one of the following expressions (I) to (IV) (hereinafter, in the components constituting the component (C), a component having an oxyethylene addition molar number of X or more is designated as ($C_X$), and a component having an oxyethylene addition molar number of X or more and Y or less is designated as ($C_{X-Y}$)).

$$(C_5)/(A) \geq 4.5 \qquad (I)$$

$$(C_{10})/(A) \geq 3.5 \qquad (II)$$

$$(C_{15})/(A) \geq 1.2 \qquad (III)$$

$$(C_{30})/(A) \geq 0.2 \qquad (IV)$$

When the hair cosmetic of the present invention contains the specified component in the component (C) in a predetermined proportion to the component (A), it hardly produces an aggregate to be caused owing to complex formation between the component (A) and the component (B) even in an alkaline region and has favorable stability.

From the viewpoint of obtaining the aforementioned effect, the hair cosmetic is preferably satisfied with at least one of the expressions (II), (III), and (IV), more preferably satisfied with at least one of the expressions (III) and (IV), and still more preferably satisfied with at least the expression (III).

From the viewpoint of suppressing the production of an aggregate, a mass ratio ($C_5$)/(A) of the component (C) to the component (A) is preferably 5.0 or more, more preferably 5.5 or more, and still more preferably 6.0 or more. In addition, from the viewpoint of suppressing a lowering of touch of the hair, the mass ratio ($C_5$)/(A) is preferably 40 or less, more preferably 30 or less, and still more preferably 20 or less.

From the viewpoint of suppressing the production of an aggregate, a mass ratio ($C_{10}$)/(A) of the component ($C_{10}$) to the component (A) is preferably 4.0 or more, more preferably 4.5 or more, and still more preferably 5.0 or more. In addition, from the viewpoint of suppressing a lowering of touch of the hair, the mass ratio ($C_{10}$)/(A) is preferably 40 or less, more preferably 30 or less, and still more preferably 20 or less.

From the viewpoint of suppressing the production of an aggregate, a mass ratio $(C_{15})/(A)$ of the component $(C_{15})$ to the component (A) is preferably 1.5 or more, more preferably 2.0 or more, still more preferably 2.5 or more, yet still more preferably 3.0 or more, and even yet still more preferably 3.5 or more. In addition, from the viewpoint of suppressing a lowering of touch of the hair, the mass ratio $(C_{15})/(A)$ is preferably 40 or less, more preferably 30 or less, and still more preferably 20 or less.

From the viewpoint of suppressing the production of an aggregate, a mass ratio $(C_{30})/(A)$ of the component $(C_{30})$ to the component (A) is preferably 0.3 or more, more preferably 0.5 or more, still more preferably 0.6 or more, yet still more preferably 0.7 or more, even yet still more preferably 0.8 or more, even still more preferably 1.0 or more, and even still more further preferably 1.5 or more. In addition, from the viewpoint of suppressing a lowering of touch of the hair, the mass ratio $(C_{30})/(A)$ is preferably 40 or less, more preferably 30 or less, and still more preferably 20 or less.

From the viewpoint of suppressing the production of an aggregate, a mass ratio $(C_{200})/(A)$ of the component $(C_{200})$ to the component (A) is preferably 5.0 or less, more preferably 4.0 or less, still more preferably 3.0 or less, yet still more preferably 2.0 or less, even yet still more preferably 1.0 or less, and even still more preferably 0.

From the viewpoint of suppressing the production of an aggregate, a mass ratio $(C_{70})/(A)$ of the component $(C_{70})$ to the component (A) is preferably 5.0 or less, more preferably 4.0 or less, still more preferably 3.0 or less, yet still more preferably 2.0 or less, even yet still more preferably 1.0 or less, and even still more preferably 0.

From the viewpoint of suppressing the production of an aggregate, a mass ratio $(C_{20\text{-}40})/(A)$ of the component $(C_{20\text{-}40})$ to the component (A) is preferably 0.2 or more, more preferably 0.5 or more, still more preferably 0.8 or more, and yet still more preferably 1.5 or more, and from the viewpoint of suppressing a lowering of touch of the hair, the mass ratio $(C_{240})/(A)$ is preferably 20 or less, more preferably 15 or less, still more preferably 10 or less, and yet still more preferably 5 or less.

From the viewpoint of suppressing the production of an aggregate and the viewpoint of emulsification stability in the case of providing an emulsion, the content of the component (C) in the hair cosmetic is preferably 0.05% by mass or more, more preferably 0.3% by mass or more, still more preferably 0.5% by mass or more, and yet still more preferably 0.7% by mass or more. In addition, from the viewpoint of suppressing a lowering of touch of the hair, the content of the component (C) in the hair cosmetic is preferably 20% by mass or less, more preferably 10% by mass or less, still more preferably 7.0% by mass or less, and yet still more preferably 5.0% by mass or less.

However, from the viewpoint of suppressing the production of an aggregate, the content of the component (C) in the hair cosmetic is preferably 0.225% by mass or more, more preferably 0.25% by mass or more, still more preferably 0.275% by mass or more, yet still more preferably 0.30% by mass or more, and even yet still more preferably 0.50% by mass or more. In addition, from the viewpoint of suppressing a lowering of touch of the hair, the content of the component (C) in the hair cosmetic is preferably 20% by mass or less, more preferably 10% by mass or less, still more preferably 7.0% by mass or less, and yet still more preferably 5.0% by mass or less.

From the viewpoint of suppressing the production of an aggregate, the content of the component $(C_{10})$ in the hair cosmetic is preferably 0.175% by mass or more, more preferably 0.20% by mass or more, still more preferably 0.225% by mass or more, yet still more preferably 0.25% by mass or more, even yet still more preferably 0.3% by mass or more, and even still more preferably 0.4% by mass or more. In addition, from the viewpoint of suppressing a lowering of touch of the hair, the content of the component $(C_{10})$ in the hair cosmetic is preferably 20% by mass or less, more preferably 10% by mass or less, still more preferably 7.0% by mass or less, and yet still more preferably 5.0% by mass or less.

From the viewpoint of suppressing the production of an aggregate, the content of the component $(C_1)$ in the hair cosmetic is preferably 0.06% by mass or more, more preferably 0.075% by mass or more, still more preferably 0.10% by mass or more, yet still more preferably 0.15% by mass or more, even yet still more preferably 0.175% by mass or more, and even still more preferably 0.20% by mass or more. In addition, from the viewpoint of suppressing a lowering of touch of the hair, the content of the component $(C_1)$ in the hair cosmetic is preferably 20% by mass or less, more preferably 10% by mass or less, still more preferably 7.0% by mass or less, and yet still more preferably 5.0% by mass or less.

From the viewpoint of suppressing the production of an aggregate, the content of the component $(C_{30})$ in the hair cosmetic is preferably 0.01% by mass or more, more preferably 0.015% by mass or more, still more preferably 0.025% by mass or more, yet still more preferably 0.030% by mass or more, even yet still more preferably 0.035% by mass or more, even still more preferably 0.04% by mass or more, even still more further preferably 0.05% by mass or more, and even yet still more further preferably 0.075% by mass or more. In addition, from the viewpoint of suppressing a lowering of touch of the hair, the content of the component $(C_{30})$ in the hair cosmetic is preferably 20% by mass or less, more preferably 10% by mass or less, still more preferably 7.0% by mass or less, and yet still more preferably 5.0% by mass or less.

From the viewpoint of suppressing the production of an aggregate, the hair cosmetic of the present invention is preferably satisfied with at least one of the following (V) to (VIII).

The content of the component $(C_5)$ in the components constituting the component (C) is 98% by mass or more   (V)

The content of the component $(C_{10})$ in the components constituting the component (C) is 75% by mass or more   (VI)

The content of the component $(C_{15})$ in the components constituting the component (C) is 30% by mass or more   (VII)

The content of the component $(C_{30})$ in the components constituting the component (C) is 0% by mass or more   (VIII)

From the viewpoint of suppressing the production of an aggregate, the hair cosmetic of the present invention is more preferably satisfied with at least one of the foregoing (VI) to (VIII), and still more preferably satisfied with at least one of the foregoing (VII) and (VIII).

In addition, from the viewpoint of suppressing the production of an aggregate, the hair cosmetic of the present invention is preferably satisfied with the following (IX).

The content of the component $(C_{200})$ in the components constituting the component (C) is 50% by mass or less   (IX)

Furthermore, from the same viewpoint, the hair cosmetic of the present invention is preferably satisfied with the following (X).

The content of the component ($C_{70}$) in the components constituting the component ($C$) is 50% by mass or less     (X)

With respect to the foregoing (V), from the viewpoint of suppressing the production of an aggregate, the content of the component (C) in the components constituting the component (C) is more preferably 98.5% by mass or more, and it is 100% by mass or less.

With respect to the foregoing (VI), from the viewpoint of suppressing the production of an aggregate, the content of the component ($C_{10}$) in the components constituting the component (C) is more preferably 80% by mass or more, still more preferably 85% by mass or more, and yet still more preferably 90% by mass or more, and it is 100% by mass or less.

With respect to the foregoing (VII), from the viewpoint of suppressing the production of an aggregate, the content of the component ($C_{15}$) in the components constituting the component (C) is more preferably 40% by mass or more, still more preferably 50% by mass or more, and yet still more preferably 60% by mass or more, and it is 100% by mass or less.

With respect to the foregoing (VIII), from the viewpoint of suppressing the production of an aggregate, the content of the component ($C_{30}$) in the components constituting the component (C) is more preferably 2.5% by mass or more, still more preferably 5% by mass or more, and yet still more preferably 10% by mass or more, and it is 100% by mass or less.

With respect to the foregoing (IX), from the viewpoint of suppressing the production of an aggregate, the content of the component ($C_{200}$) in the components constituting the component (C) is preferably 30% by mass or less, more preferably 10% by mass or less, still more preferably 5% by mass or less, and yet still more preferably 0% by mass.

With respect to the foregoing (X), from the viewpoint of suppressing the production of an aggregate, the content of the component ($C_{70}$) in the components constituting the component (C) is preferably 30% by mass or less, more preferably 10% by mass or less, still more preferably 5% by mass or less, and yet still more preferably 0% by mass.

From the viewpoint of suppressing the production of an aggregate and the viewpoint of emulsification stability in the case of providing an emulsion, in the hair cosmetic, a mass ratio of the component (C) to the component (A) and component (B) $\{(C)/[(A)+(B)]\}$ is preferably 10 or less, more preferably 8.0 or less, still more preferably 6.0 or less, and yet still more preferably 5.0 or less. In addition, from the viewpoint of suppressing the production of an aggregate, the mass ratio $(C)/[(A)+(B)]$ is preferably 0.2 or more, more preferably 0.3 or more, still more preferably 0.5 or more, yet still more preferably 1.0 or more, and even yet still more preferably 2.0 or more.

From the viewpoint of suppressing the production of an aggregate, the hair cosmetic of the present invention is preferably satisfied with at least one of the following expressions (XI) to (XIV).

Mass ratio $(C_5)/[(A)+(B)] \geq 0.2$     (XI)

Mass ratio $(C_{10})/[(A)+(B)] \geq 0.2$     (XII)

Mass ratio $(C_{15})/[(A)+(B)] \geq 0.2$     (XIII)

Mass ratio $(C_{30})/[(A)+(B)] \geq 0.01$     (XIV)

From the viewpoint of suppressing the production of an aggregate, the hair cosmetic of the present invention is more preferably satisfied with at least one of the foregoing (XII) to (XIV), and still more preferably satisfied with at least one of the foregoing (XIII) and (XIV).

From the viewpoint of improvement in touch of the hair, in the hair cosmetic of the present invention, the mass ratio of the component (C) to the component (A) and component (B) $\{(C_5)/[(A)+(B)]\}$ is preferably 10 or less, more preferably 8.0 or less, still more preferably 6.0 or less, and yet still more preferably 5.0 or less. In addition, from the viewpoint of suppressing the production of an aggregate, the mass ratio $(C_5)/[(A)+(B)]$ is more preferably 0.5 or more, still more preferably 1.0 or more, yet still more preferably 2.25 or more, even yet still more preferably 2.5 or more, and even still more preferably 2.75 or more.

From the viewpoint of improvement in touch of the hair, in the hair cosmetic of the present invention, the mass ratio $\{(C_{10})/[(A)+(B)]\}$ of the component ($C_{10}$) to the component (A) and component (B) is preferably 6.0 or less, more preferably 5.5 or less, and still more preferably 5.0 or less. In addition, from the viewpoint of suppressing the production of an aggregate, the mass ratio $(C_{10})/[(A)+(B)]$ is more preferably 0.4 or more, still more preferably 1.75 or more, yet still more preferably 2.0 or more, and even yet still more preferably 2.25 or more.

From the viewpoint of improvement in touch of the hair, in the hair cosmetic of the present invention, the mass ratio $\{(C_{15})/[(A)+(B)]\}$ of the component ($C_1$) to the component (A) and component (B) is preferably 6.0 or less, more preferably 5.0 or less, and still more preferably 4.0 or less. In addition, from the viewpoint of suppressing the production of an aggregate, the mass ratio $(C_1)/[(A)+(B)]$ is more preferably 0.4 or more, still more preferably 0.6 or more, yet still more preferably 0.75 or more, and even yet still more preferably 1.0 or more.

From the viewpoint of improvement in touch of the hair, in the hair cosmetic of the present invention, the mass ratio of the component ($C_{30}$) to the component (A) and component (B) $\{(C_{30})/[(A)+(B)]\}$ is preferably 5.5 or less, more preferably 5.0 or less, and still more preferably 4.0 or less. In addition, from the viewpoint of suppressing the production of an aggregate, the mass ratio $(C_{30})/[(A)+(B)]$ is more preferably 0.05 or more, still more preferably 0.1 or more, yet still more preferably 0.15 or more, and even yet still more preferably 0.25 or more.

In addition, from the viewpoint of improvement in touch of the hair and the viewpoint of suppressing the production of an aggregate, in the hair cosmetic of the present invention, the mass ratio of the component ($C_{200}$) to the component (A) and component (B) $\{(C_{200})/[(A)+(B)]\}$ is preferably 3.0 or less, more preferably 2.0 or less, still more preferably 1.0 or less, and yet still more preferably 0.

Furthermore, from the viewpoint of improvement in touch of the hair and the viewpoint of suppressing the production of an aggregate, in the hair cosmetic of the present invention, the mass ratio of the component ($C_{70}$) to the component (A) and component (B) $\{(C_{70})/[(A)+(B)]\}$ is preferably 3.0 or less, more preferably 2.0 or less, still more preferably 1.0 or less, and yet still more preferably 0.

Although the hair cosmetic of the present invention may contain other nonionic surfactant than the component (C) within a range where the effects of the present invention are not impaired, the content thereof is preferably 5% by mass or less, more preferably 2% by mass or less, still more preferably 1% by mass or less, and yet still more preferably 0.5% by mass or less in the hair cosmetic.

<pH>

From the viewpoint of enhancing penetration properties of the component (A) in the hair and improving the hair dyeing properties, the pH of the hair cosmetic of the present invention is 8.0 or more, preferably 8.5 or more, and more preferably 9.0 or more. The component (A) that is a melanin precursor reacts with oxygen in air under a basic condition and is readily converted to a melanin pigment, and therefore, when the pH is 8.0 or more, the hair dyeing properties are improved. In addition, the pH is 12.0 or less, and from the viewpoint of improvement in hair dyeing properties and suppressing a damage on the hair, the pH is preferably 11.0 or less, and more preferably 10.5 or less.

The aforementioned pH is a measured value at 25° C., and specifically, it can be measured by a method described in the section of Examples.

(Alkaline Agent)

It is preferred that the hair cosmetic of the present invention contains an alkaline agent. The alkaline agent has not only an action to swell the hair, thereby opening the cuticle and penetrating a dyeing agent, such as the component (A), into the interior of the hair, but also an action to promote a polymerization reaction of the component (A), thereby improving the hair dyeing properties. As the alkaline agent, any material can be used without particular limitations so long as it is an alkaline agent that is used for usual hair dyes.

Examples of the alkaline agent include ammonia; alkanolamines, such as mono-, di-, or tri-methanolamine and mono-, di-, or tri-ethanolamine; alkylamines, such as methylamine, dimethylamine, ethylamine, diethylamine, N-methylethylamine, propylamine, and butylamine; aralkylamines, such as benzylamine; and inorganic alkaline compounds, such as sodium hydroxide and potassium hydroxide, and one or more of these materials can be used. The carbon number of the alkanolamine, alkylamine, or aralkylamine is preferably 10 or less, and more preferably 8 or less from the viewpoint of water solubility.

Above all, from the viewpoint of hair dyeing properties, the alkaline agent is preferably one or more selected from the group consisting of ammonia, an alkanolamine, an alkylamine, an aralkylamine, sodium hydroxide, and potassium hydroxide. The hair cosmetic of the present invention more preferably contains one or more of ammonia and an alkanolamine, still more preferably contains a monoalkanolamine, and yet still more preferably contains monoethanolamine.

From the viewpoint of improvement in hair dyeing properties, the content of the alkaline agent in the hair cosmetic is preferably 0.01% by mass or more, more preferably 0.1% by mass or more, and still more preferably 0.5% by mass or more, and from the viewpoint of suppressing irritation, it is preferably 10% by mass or less, more preferably 7.5% by mass or less, and still more preferably 5% by mass or less.

(Antioxidant)

Examples of the antioxidant include sulfurous acid, ascorbic acid, thioglycolic acid, L-cysteine, and N-acetyl-L-cysteine, and salts thereof. From the viewpoint of stabilization of the component (A) and improvement in hair dyeing properties, sulfurous acid, ascorbic acid, or a salt thereof is preferred.

In the case of using the antioxidant, its content in the hair cosmetic is preferably 0.01% by mass or more, and more preferably 0.05% by mass or more, and it is preferably 10% by mass or less, more preferably 5% by mass or less, and still more preferably 2% by mass or less.

(pH Adjustor)

From the viewpoint of adjusting the pH to an optimum range for polymerization of the component (A), thereby improving the hair dyeing properties, the hair cosmetic of the present invention can contain a pH adjustor. In the case where the hair cosmetic contains the aforementioned alkaline agent, a protonating agent is preferred as the pH adjustor. The protonating agent may be any of a monobasic acid and a polybasic acid, and may be any of an organic acid (the carbon number is 1 or more and 8 or less, provided that ascorbic acid is excluded) and an inorganic acid. As the protonating agent, one or more selected from the group consisting of hydrochloric acid, sulfuric acid, phosphoric acid, formic acid, acetic acid, and citric acid are exemplified, and one or two selected from the group consisting of phosphoric acid and citric acid are more preferred.

In the case of using the pH adjustor, though the content thereof is not particularly limited so long as it is an amount at which the pH of the hair cosmetic can be adjusted to a desired range, it is preferably 0.05% by mass or more, more preferably 0.1% by mass or more, and still more preferably 0.2% by mass or more. In addition, from the viewpoint of formulation stability, the content of the pH adjustor is preferably 5.0% by mass or less, more preferably 4.0% by mass or less, and still more preferably 3.5% by mass or less.

<Other Components>

The hair cosmetic of the present invention may appropriately contain, in addition to the aforementioned components, a component which is usually used for hair cosmetics, within a range where the purpose of the present invention is not impaired. Examples of the foregoing component include a higher alcohol, an oil, a dyeing agent other than the component (A), a polymer, an aromatic alcohol, an anti-dandruff agent, a vitamin compound, a disinfectant, an antiinflammatory agent, an antiseptic, a chelating agent, a humectant, a pearlescent agent, a ceramide, a perfume, and an ultraviolet absorber.

(Higher Alcohol)

The hair cosmetic of the present invention can contain a higher alcohol. In the case where the hair cosmetic is a hair cosmetic selected from the group consisting of a hair rinse, a hair conditioning agent, and a hair treatment agent, emulsification stability is improved.

As the higher alcohol, one represented by a general formula: $R^{21}$—OH [wherein $R^{21}$ represents a linear or branched hydrocarbon group having 12 or more and 24 or less carbon atoms] can be used. $R^{21}$ is preferably a linear or branched aliphatic hydrocarbon group having 12 or more and 24 or less carbon atoms; more preferably a linear or branched alkyl group having 12 or more and 24 or less carbon atoms or a linear or branched alkenyl group having 12 or more and 24 or less carbon atoms; and still more preferably a linear alkyl group having 12 or more and 24 or less carbon atoms or a linear alkenyl group having 12 or more and 24 or less carbon atoms.

Examples of the higher alcohol include lauryl alcohol, myristyl alcohol, cetyl alcohol, stearyl alcohol, isostearyl alcohol, arachidyl alcohol, behenyl alcohol, carnaubyl alcohol, and oleyl alcohol. The higher alcohol can be used alone or in combination of two or more thereof.

From the viewpoint of controlling a change in viscosity with a lapse of time of the hair cosmetic, the higher alcohol is preferably a combination of (1a) one in which $R^{21}$ in the aforementioned general formula is a linear alkyl group having 12 or more and 18 or less carbon atoms with (1b) one in which $R^{21}$ is a linear alkyl group having 20 or more and 24 or less carbon atoms; and more preferably a combination of (1a) one in which R²¹ is a linear alkyl group having 14 or more and 18 or less carbon atoms with (1b) one in which R²¹ is a linear alkyl group having 20 or more and 22 or less carbon atoms. From the viewpoint of controlling a change in viscosity with a lapse of time, a mass ratio of the component (1a) to the component (1b) [(1a)/(1b)] is preferably 5/95 to 95/5, more preferably 10/90 to 90/10, still more preferably 15/85 to 85/15, and yet still more preferably 20/80 to 80/20.

In the case where the hair cosmetic contains the higher alcohol, from the viewpoint of improvement in emulsification stability, the content thereof is preferably 3% by mass or more, more preferably 4% by mass or more, and still more preferably 5% by mass or more, and it is preferably 12% by mass or less, more preferably 11% by mass or less, still more preferably 10% by mass or less, and yet still more preferably 8% by mass or less.

When the content of the higher alcohol in the hair cosmetic is less than 3% by mass, in the case where in the component (C), a component having an oxyethylene addition molar number of less than 5 is designated as ($C_{<5}$), from the viewpoint of suppressing the production of an aggregate, the content of the component ($C_{<5}$) in the component (C) is preferably 5% by mass or less, more preferably 3% by mass or less, still more preferably 2% by mass or less, and yet still more preferably 1.5% by mass or less.

(Oil)

From the viewpoint of improvement in touch of the hair, the hair cosmetic of the present invention can contain an oil. Examples of the oil include hydrocarbons, such as squalene, squalane, liquid paraffin, liquid isoparaffin, and cycloparaffin; glycerides, such as castor oil, cacao oil, mink oil, avocado oil, and olive oil; waxes, such as beeswax, spermaceti wax, lanolin, and carnauba wax; esters, such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids, such as capric acid, lauric acid, myristic acid, palmitic acid, stearic acid, behenic acid, oleic acid, coconut oil fatty acid, isostearic acid, and isopalmitic acid; and besides, isostearyl glyceryl ether and polyoxypropylene butyl ether. The oil can be used alone or in combination of two or more thereof.

In the case where the hair cosmetic contains the oil, from the viewpoint of improvement in touch of the hair, the content thereof is preferably 0.2% by mass or more, more preferably 0.3% by mass or more, and still more preferably 0.5% by mass or more, and from the viewpoint of suppressing a lowering of touch of the hair, it is preferably 10% by mass or less, more preferably 8% by mass or less, and still more preferably 5% by mass or less.

(Dyeing Agent Other than Component (A))

The hair cosmetic of the present invention may further contain a dyeing agent other than the component (A). Examples of the foregoing dyeing agent include an oxidation dye (constituted of a precursor and a coupler) and a direct dye, each of which is typically used for hair dyes.

As the dying agent other than the component (A), one or more materials can be used. The foregoing dyeing agent is preferably an oxidation dye. As the precursor, paraphenylenediamine, toluene-2,5-diamine, paraaminophenol, 4-aminomnetacresol, 1-hydroxyethiyl-45-diaminopyrazole, and salts thereof are preferred; and as the coupler, 2,4-diaminophenoxyethanol, metaaminophenol, 2-methyl-5-aminophenol [=5-aminoorthocresol], resorcin, 2-methylresorcin, 4-chlororesorcinol, 1-naphthol, 2-amino-3-hydroxypyridine, 2-amino-4-(β-hydroxyethyl) aminoanisole, and salts thereof are preferred. In the case of using the dyeing agent other than the component (A), the content thereof in the hair cosmetic is preferably 0.01% by mass or more, and more preferably 0.02% by mass or more, and it is preferably 1% by mass or less, and more preferably 0.5% by mass or less.

(Aqueous Medium)

The hair cosmetic typically contains an aqueous medium. Examples of the aqueous medium include water; a lower alcohol, such as ethanol and isopropyl alcohol; and a low-molecular diol or triol having 6 or less carbon atoms, such as 1,3-butylene glycol, glycerin, ethylene glycol, and propylene glycol, with water being preferred. Although the content of the aqueous medium in the hair cosmetic can be appropriately selected according to the formulation of the hair cosmetic, it is typically in a range of 1 to 95% by mass. In the case of using water as the aqueous medium, from the viewpoint of easiness of applying the hair cosmetic on the hair, stability in the case of being formed in an emulsified state, and revealing high hair dyeing properties, the content of water in the hair cosmetic is preferably 50% by mass or more, more preferably 0% by mass or more, and still more preferably 70% by mass, and it is preferably 95% by mass or less, and more preferably 90% by mass or less.

A production method of the hair cosmetic of the present invention is not particularly limited. For example, the hair cosmetic of the present invention can be produced by blending the components (A) to (C), and other components which are used, if desired by a method described in the section of Examples and mixing the blend by using a known stirring device or the like.

[Dyeing Method of Hair]

The present invention further provides a dyeing method of hair including a step of applying the aforementioned hair cosmetic on hair. For example, as the dyeing method of hair, in the case where the hair cosmetic is a hair conditioning agent, a hair treatment agent, or a hair dye, the foregoing hair cosmetic is applied on hair and then allowed to stand for a short time (about 1 to 5 minutes), as the need arises, followed by cleansing away. By daily repeating the foregoing step, dyeing of a gray hair or the like can be easily performed.

Regarding the aforementioned embodiments, the present invention discloses the following hair cosmetics and dyeing methods of hair.

<1> A hair cosmetic containing the following components (A) to (C):

(A) a compound represented by the following general formula (1) or a salt thereof:

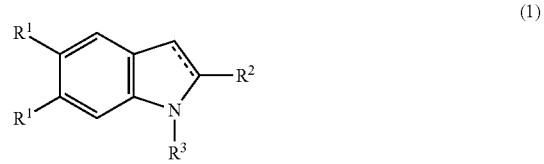

(1)

wherein a broken line represents the presence or absence of a π bond; R¹ represents a hydroxy group or an acetoxy group; R² represents a hydrogen atom or —COOR (R is a hydrogen atom, a methyl group, or an ethyl group); and R³ represents a hydrogen atom, an acetyl group, a methyl group, or an ethyl group;

(B) a cationic surfactant; and
(C) a polyoxyethylene addition type nonionic surfactant,
wherein
a mass ratio of the component (B) to the component (A) [(B)/(A)] is 1.0 or more, and a mass ratio of the component (C) to the component (A) [(C)/(A)] is 1.0 or more;
when in components constituting the component (C), a component having an oxyethylene addition molar number of 5 or more is designated as (C), a component having an oxyethylene addition molar number of 10 or more is designated as ($C_{10}$), a component having an oxyethylene addition molar number of 15 or more is designated as ($C_{15}$), and a component having an oxyethylene addition molar number of 30 or more is designated as ($C_{30}$), a mass ratio of each of the components relative to the component (A) is satisfied with at least one of the following expressions (I) to (IV); and
a pH at 25° C. of the hair cosmetic is 8.0 or more and 12.0 or less:

$$40 \geq (C_5)/(A) \geq 4.5 \qquad (I)$$

$$40 \geq (C_{10})/(A) \geq 3.5 \qquad (II)$$

$$40 \geq (C_{15})/(A) \geq 1.2 \qquad (III)$$

$$40 \geq (C_{30})/(A) \geq 0.2 \qquad (IV)$$

<2> A hair cosmetic containing the following components (A) to (C):
(A) a compound represented by the following general formula (1) or a salt thereof:

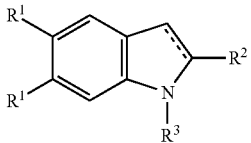

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;
(B) a cationic surfactant; and
(C) a polyoxyethylene addition type nonionic surfactant,
wherein
a mass ratio of the component (B) to the component (A) [(B)/(A)] is 1.0 to 20, and a mass ratio of the component (C) to the component (A) [(C)(A)] is 1.0 to 30;
when in components constituting the component (C), a component having an oxyethylene addition molar number of 5 or more is designated as (C), a component having an oxyethylene addition molar number of 10 or more is designated as ($C_{10}$), a component having an oxyethylene addition molar number of 15 or more is designated as ($C_1$), a component having an oxyethylene addition molar number of 30 or more is designated as ($C_{30}$), and a component having an oxyethylene addition molar number of 200 or more is designated as ($C_{200}$), a mass ratio of each of the components relative to the component (A) is satisfied with at least one of the following expressions (I) to (IV), and ($C_{200}$)/(A) is satisfied with 5.0 or less; and a pH at 25° C. of the hair cosmetic is 8.0 or more and 12.0 or less:

$$40 \geq (C_5)/(A) \geq 4.5 \qquad (I)$$

$$40 \geq (C_{10})/(A) \geq 3.5 \qquad (II)$$

$$40 \geq (C_{15})/(A) \geq 1.2 \qquad (III)$$

$$40 \geq (C_{30})/(A) \geq 0.2 \qquad (IV)$$

<3> A hair cosmetic containing the following components (A) to (C):
(A) a compound represented by the following general formula (1) or a salt thereof:

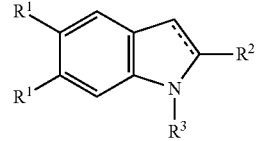

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;
(B) a cationic surfactant; and
(C) a polyoxyethylene addition type nonionic surfactant,
wherein
a mass ratio of the component (B) to the component (A) [(B)/(A)] is 1.5 or more, and a mass ratio of the component (C) to the component (A) [(C)/(A)] is 2.5 or more and 30 or less;
when in components constituting the component (C), a component having an oxyethylene addition molar number of 5 or more is designated as ($C_5$), a component having an oxyethylene addition molar number of 10 or more is designated as ($C_{10}$), a component having an oxyethylene addition molar number of 15 or more is designated as (C), and a component having an oxyethylene addition molar number of 30 or more is designated as ($C_{30}$), a mass ratio of each of the components relative to the component (A) is satisfied with at least one of the following expressions (I) to (IV), the mass ratio of the component ($C_1$) to the component (A) and component (B) $\{(C_{15})/[(A)+(B)]\}$ is 0.4 or more and 4.0 or less, and the content of the component ($C_{13}$) in the components constituting the component (C) is 30% by mass or more; and
a pH at 25° C. of the hair cosmetic is 8.0 or more and 12.0 or less:

$$30 \geq (C_5)/(A) \geq 4.5 \qquad (I)$$

$$30 \geq (C_{10})/(A) \geq 3.5 \qquad (II)$$

$$30 \geq (C_{15})/(A) \geq 1.2 \qquad (III)$$

$$30 \geq (C_{30})/(A) \geq 0.2 \qquad (IV)$$

<4> A hair cosmetic containing the following components (A) to (C):
(A) a compound represented by the following general formula (1) or a salt thereof:

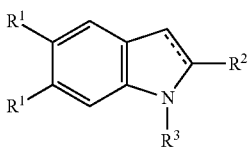

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a cationic surfactant; and (C) a polyoxyethylene addition type nonionic surfactant, wherein a mass ratio of the component (B) to the component (A) [(B)/(A)] is 1.5 or more and 20 or less, and a mass ratio of the component (C) to the component (A) [(C)/(A)] is 2.5 or more and 25 or less;

when in components constituting the component (C), a component having an oxyethylene addition molar number of 5 or more is designated as ($C_5$), a component having an oxyethylene addition molar number of 10 or more is designated as ($C_{10}$), a component having an oxyethylene addition molar number of 15 or more is designated as ($C_{15}$), and a component having an oxyethylene addition molar number of 30 or more is designated as ($C_{30}$), a mass ratio of each of the components relative to the component (A) is satisfied with at least one of the following expressions (I) to (IV), the mass ratio of the component ($C_{15}$) to the component (A) and component (B) {(C)/[(A)+(B)]} is 0.4 or more and 4.0 or less, and the content of the component ($C_{15}$) in the components constituting the component (C) is 50% by mass or more and 100% by mass or less; and a pH at 25° C. of the hair cosmetic is 8.0 or more and 12.0 or less:

$$20 \geq (C_5)/(A) \geq 4.5 \quad (I)$$

$$20 \geq (C_{10})/(A) \geq 3.5 \quad (II)$$

$$20 \geq (C_{15})/(A) \geq 1.2 \quad (III)$$

$$20 \geq (C_{30})/(A) \geq 0.2 \quad (IV)$$

<5> The hair cosmetic as set forth in any one of <1> to <4>, wherein the component (B) is a mono- or di-long chain alkyl quaternary ammonium salt represented by the following general formula:

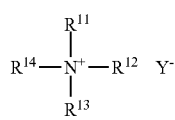

wherein $R^{11}$ represents a linear or branched alkyl group having 8 or more and 22 or less carbon atoms, or a group represented by $R^{15}CONH(CH_2)_m$—, $R^{15}$—O—$(CH_2)_m$—, or $R^{15}COO(CH_2)_m$— ($R^{15}$ represents a linear or branched alkyl group having 7 or more and 21 or less carbon atoms, and m represents a number of 1 or more and 4 or less); $R^{12}$ represents a linear or branched alkyl group having 1 or more and 22 or less carbon atoms, or a group represented by the foregoing $R^{15}CONH(CH_2)_m$—, $R^{15}$—O—$(CH_2)_m$—, or $R^{15}COO(CH_2)_m$—; $R^{13}$ and $R^{14}$ each independently represent an alkyl group having 1 or more and 4 or less carbon atoms; and $Y^-$ represents a chloride ion, a bromide ion, or a methosulfate ion.

<6> The hair cosmetic as set forth in any one of <1> to <5>, wherein the component (C) is a polyoxyethylene alkyl ether.

<7> The hair cosmetic as set forth in any one of <1> to <6>, which is not only satisfied with at least one of the following (V) to (VIII) but also satisfied with the following (IX):

The content of the component ($C_5$) in the components constituting the component (C) is 98% by mass or more and 100% by mass or less (V)

The content of the component ($C_{10}$) in the components constituting the component (C) is 75% by mass or more and 100% by mass or less (VI)

The content of the component ($C_{15}$) in the components constituting the component (C) is 30% by mass or more and 100% by mass or less (VII)

The content of the component ($C_{30}$) in the components constituting the component (C) is 0% by mass or more and 100% by mass or less (VIII)

The content of the component ($C_{200}$) in the components constituting the component (C) is 10% by mass or less (IX)

<8> The hair cosmetic as set forth in any one of <1> to <7>, which is not only satisfied with at least one of the following (V) to (VIII) but also satisfied with the following (X):

The content of the component ($C_5$) in the components constituting the component (C) is 98% by mass or more and 100% by mass or less (V)

The content of the component ($C_{10}$) in the components constituting the component (C) is 75% by mass or more and 100% by mass or less (VI)

The content of the component ($C_{15}$) in the components constituting the component (C) is 30% by mass or more and 100% by mass or less (VII)

The content of the component ($C_{30}$) in the components constituting the component (C) is 0% by mass or more and 100% by mass or less (VIII)

The content of the component ($C_{70}$) in the components constituting the component (C) is 10% by mass or less (X)

<9> The hair cosmetic as set forth in any one of <1> to <8>, wherein when the content of a higher alcohol in the hair cosmetic is less than 3% by mass, in the case where in the components constituting the component (C), a component having an oxyethylene addition molar number of less than 5 is designated as ($C_{<5}$), the content of the component ($C_{<5}$) in the component (C) is 5% by mass or less.

<10> The hair cosmetic as set forth in any one of <1> to <9>, wherein the content of the component (A) is 0.05% by mass or more and 5% by mass or less.

<11> A hair cosmetic containing the following components (A) to (C):

(A) a compound represented by the following general formula (1) or a salt thereof:

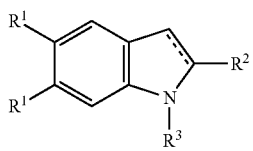

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) one or more selected from a monoalkyltrimethylammonium chloride and a monoalkyloxyalkyltrimethylammonium chloride; and (C) a polyoxyethylene alkyl ether, wherein a mass ratio of the component (B) to the component (A) [(B)/(A)] is 1.0 to 20, and a mass ratio of the component (C) to the component (A) [(C)(A)] is 1.0 to 30;

when in components constituting the component (C), a component having an oxyethylene addition molar number of 5 or more is designated as ($C_5$), a component having an oxyethylene addition molar number of 10 or more is designated as ($C_{10}$), a component having an oxyethylene addition molar number of 15 or more is designated as ($C_{15}$), a component having an oxyethylene addition molar number of 30 or more is designated as ($C_{30}$), and a component having an oxyethylene addition molar number of 200 or more is designated as ($C_{200}$), a mass ratio of each of the components relative to the component (A) is satisfied with at least one of the foregoing expressions (I) to (IV), and ($C_{200}$)/(A) is satisfied with 5.0 or less; and a pH at 25° C. of the hair cosmetic is 8.0 or more and 12.0 or less.

<12> A hair cosmetic containing the following components (A) to (C):

(A) a compound represented by the following general formula (1) or a salt thereof:

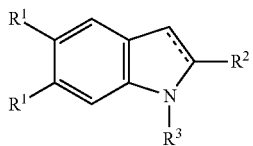

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) one or more selected from a monoalkyltrimethylammonium chloride and a monoalkyloxyalkyltrimethylammonium chloride; and (C) a polyoxyethylene alkyl ether, wherein a mass ratio of the component (B) to the component (A) [(B)/(A)] is 1.0 to 20, and a mass ratio of the component (C) to the component (A) [(C)(A)] is 1.0 to 30;

when in components constituting the component (C), a component having an oxyethylene addition molar number of 5 or more is designated as ($C_5$), a component having an oxyethylene addition molar number of 10 or more is designated as ($C_{10}$), a component having an oxyethylene addition molar number of 15 or more is designated as ($C_{15}$), a component having an oxyethylene addition molar number of 30 or more is designated as ($C_{30}$), and a component having an oxyethylene addition molar number of 200 or more is designated as ($C_{200}$), a mass ratio of each of the components relative to the component (A) is satisfied with at least one of the following expressions (I) to (IV), and ($C_{70}$)/(A) is satisfied with 5.0 or less; and a pH at 25° C. of the hair cosmetic is 8.0 or more and 12.0 or less.

<13> The hair cosmetic as set forth in <11> or <12>, which is not only satisfied with at least one of the following (V) to (VIII) but also satisfied with the following (IX):

The content of the component ($C_5$) in the components constituting the component (C) is 98% by mass or more and 100% by mass or less     (V)

The content of the component ($C_{10}$) in the components constituting the component (C) is 75% by mass or more and 100% by mass or less     (VI)

The content of the component ($C_{15}$) in the components constituting the component (C) is 30% by mass or more and 100% by mass or less     (VII)

The content of the component ($C_{30}$) in the components constituting the component (C) is more than 0% by mass and 100% by mass or less     (VIII)

The content of the component ($C_{200}$) in the components constituting the component (C) is 10% by mass or less     (IX)

<14> The hair cosmetic as set forth in any one of <11> to <13>, which is not only satisfied with at least one of the following (V) to (VIII) but also satisfied with the following (X):

The content of the component ($C_5$) in the components constituting the component (C) is 98% by mass or more and 100% by mass or less     (V)

The content of the component ($C_{10}$) in the components constituting the component (C) is 75% by mass or more and 100% by mass or less     (VI)

The content of the component ($C_{15}$) in the components constituting the component (C) is 30% by mass or more and 100% by mass or less     (VII)

The content of the component ($C_{30}$) in the components constituting the component (C) is more than 0% by mass and 100% by mass or less     (VIII)

The content of the component ($C_{70}$) in the components constituting the component (C) is 10% by mass or less     (X)

<15> The hair cosmetic asset forth in anyone of <11> to <14>, wherein when the content of a higher alcohol in the hair cosmetic is less than 3% by mass, in the case where in the components constituting the component (C), a component having an oxyethylene addition molar number of less than 5 is designated as ($C_{<5}$), the content of the component ($C_{<5}$) in the component (C) is 5% by mass or less.

<16> The hair cosmetic as set forth in any one of <11> to <15>, wherein the content of the component (A) is 0.05% by mass or more and 5% by mass or less.
<17> The hair cosmetic as set forth in any one of <11> to <16>, wherein a mass ratio of a component ($C_{20-40}$) to the component (A) ($C_{20-40}$)/(A) is 0.2 or more and 20 or less.
<18> The hair cosmetic asset forth in anyone of <1> to <17>, wherein the pH at 25° C. is 8.5 or more and 11.5 or less.
<19> The hair cosmetic asset forth in anyone of <1> to <18>, wherein the pH at 25° C. is 9.0 or more and 11.0 or less.
<20> The hair cosmetic as set forth in any one of <1> to <19>, which is selected from the group consisting of a hair rinse, a hair conditioning agent, and a hair treatment agent.
<21> A dyeing method of hair including a step of applying the hair cosmetic as set forth in any one of <1> to <20> on hair.

EXAMPLES

The present invention is hereunder described by reference to Examples, but it should be construed that the present invention is not limited to the scope of the Examples.
[pH Measurement]
A pH at 25° C. of the hair cosmetic was measured with a pH meter (F-51, manufactured by HORIBA, Ltd.).
[Measurement of Oxyethylene Addition Molar Number]
The oxyethylene addition molar number of a component constituting the polyoxyethylene addition type nonionic surfactant (component (C)) was measured by the following method.
2 g of a polyoxyethylene addition type nonionic surfactant was dissolved in 10 mL of acetonitrile and analyzed through high performance liquid chromatography (Agilent 1260 Infinity, manufactured by Agilent Technologies) under the following condition.
 Column: Wakopak Wakosil-II 5SIL-AQ (4.6×250 mm, particle diameter: 5 mm) (manufactured by Wako Pure Chemical Industries, Ltd.)
 Injection amount: 5 µL
 Flow rate: 1 mL/min
 Eluting solution A: Water
 Eluting solution B: Acetonitrile (gradient)
 Detection: Charged aerosol detector (manufactured by Thermo Fisher Scientific)
 Oven temperature: 40° C.
 Condition of eluting solution
Using water as the eluting solution A and acetonitrile as the eluting solution B, the analysis was performed while changing a ratio of the eluting solution B in the following ratio (from 100% to 50%) and applying a gradient.
<One Having an Oxyethylene Average Addition Molar Number of about 10>
 Up to 3 minutes after commencement of the measurement:
 To flow 100% of the eluting solution B.
 3 to 60 minutes after commencement of the measurement:
 To flow while applying the gradient of from 100% of the eluting solution B to [(0% of the eluting solution A)/(90% of the eluting solution B)].
 60 to 70 minutes after commencement of the measurement:
 To keep at [(10% of the eluting solution A)/(90% of the eluting solution B)].

<One Having an Oxyethylene Average Addition Molar Number of about 15 to 20>
 Up to 60 minutes after commencement of the measurement:
 To flow while applying the gradient of from 100% of the eluting solution B to [(10% of the eluting solution A)/(90% of the eluting solution B)].
 60 to 180 minutes after commencement of the measurement:
 To keep at [(10% of the eluting solution A)/(90% of the eluting solution B)].
<One Having an Oxyethylene Average Addition Molar Number of about 40>
 Up to 3 minutes after commencement of the measurement:
 To flow [(15% of the eluting solution A)/(85% of the eluting solution B)].
 3 to 120 minutes after commencement of the measurement:
 To flow while applying the gradient of from [(15% of the eluting solution A)/(85% of the eluting solution B)] to [(25% of the eluting solution A)/(75% of the eluting solution B)].
 120 to 150 minutes after commencement of the measurement:
 To keep at [(25% of the eluting solution A)/(75% of the eluting solution B)].
[Calculation of Component Composition Contained in Nonionic Surfactant]
A mass ratio of every oxyethylene addition molar number of the component constituting the component (C) was calculated from a peak area ratio of the obtained chart.

Examples 1 to 16 and Comparative Examples 1 to 9

(Preparation of Hair Cosmetic)
Among the blending components shown in Tables 1 and 2, other components than ascorbic acid and the component (A) and a part of water were mixed to prepare aqueous solutions. Furthermore, ascorbic acid and a solution of the component (A) were added in a nitrogen atmosphere, to prepare hair cosmetics. All of the hair cosmetics had a pH at 25° C. of 10.2.

{Stability Evaluation 1 of Hair Cosmetic}
The stability evaluation 1 of the hair cosmetic was performed in a manner in which 10 g of the hair cosmetic prepared by the aforementioned method was charged in a 15.5-mL sample bottle and allowed to stand at 25° C. for 1 hour, and the presence or absence of a deposit and transparency were visually confirmed. The evaluation criteria are as follows.
A: A deposit is not perceived at all, and the resulting hair cosmetic is uniform and transparent.
B: A state where the resulting hair cosmetic is opaque, and a deposit is perceived but minute, and is uniformly dispersed.
C: A state where a deposit is perceived and aggregated, and it locally exists, or a precipitate is formed.

TABLE 1

|  |  | Component name | Example 1 | Example 2 | Example 3 | Example 4 | Example 5 | Example 6 | Example 7 |
|---|---|---|---|---|---|---|---|---|---|
| Blend (% by mass) | (A) | (A1) 5,6-Dihydroxyindole solution *1 | 25.00 | 25.00 | 25.00 | 25.00 | 25.00 | 25.00 | 25.00 |
|  | (B) | Stearyltrimethylammomum chloride (28%) *2 | 2.10 | 2.10 | 2.10 | 2.10 | 2.10 | 2.10 | 2.10 |
|  | (C) | Polyoxyethylene (15) cetyl ether *3 | 1.15 |  |  |  |  |  |  |
|  |  | Polyoxyethylene (20) cetyl ether *4 |  | 1.15 | 0.60 | 0.45 | 0.35 |  |  |
|  |  | Polyoxyethylene (40) cetyl ether *5 |  |  |  |  |  | 1.15 |  |
|  |  | Polyoxyethylene (150) cetyl ether *6 |  |  |  |  |  |  | 1.15 |
|  |  | Polyoxyethylene (10) cetyl ether *7 |  |  |  |  |  |  |  |
|  |  | Polyoxyethylene (2) cetyl ether *8 |  |  |  |  |  |  |  |
|  | Nonionic surfactant | Decyl glucoside (40%) *9 |  |  |  |  |  |  |  |
|  | Others | Monoethanolamine *10 | 3.00 | 3.00 | 3.00 | 3.00 | 3.00 | 3.00 | 3.00 |
|  |  | Ascorbic acid *11 | 0.10 | 0.10 | 0.10 | 0.10 | 0.10 | 0.10 | 0.10 |
|  |  | Phosphoric acid (75%) *12 | 1.10 | 1.10 | 1.10 | 1.10 | 1.10 | 1.10 | 1.10 |
|  |  | Water | 67.55 | 67.55 | 68.10 | 68.25 | 68.35 | 67.55 | 67.55 |
|  | Total |  | 100.00 | 100.00 | 100.00 | 100.00 | 100.00 | 100.00 | 100.00 |
| pH |  |  | 10.2 | 10.2 | 10.2 | 10.2 | 10.2 | 10.2 | 10.2 |
| Amount of active component (% by mass) | | Component (A) | 0.29 | 0.29 | 0.29 | 0.29 | 0.29 | 0.29 | 0.29 |
|  |  | Component (B) | 0.59 | 0.59 | 0.59 | 0.59 | 0.59 | 0.59 | 0.59 |
|  |  | Component (C) | 1.15 | 1.15 | 0.60 | 0.45 | 0.35 | 1.15 | 1.15 |
|  |  | Component ($C_5$) | 1.14 | 1.15 | 0.60 | 0.45 | 0.35 | 1.15 | 1.15 |
|  |  | Component ($C_{10}$) | 1.08 | 1.15 | 0.60 | 0.45 | 0.35 | 1.15 | 1.15 |
|  |  | Component ($C_{15}$) | 0.75 | 1.12 | 0.59 | 0.44 | 0.34 | 1.15 | 1.15 |
|  |  | Component ($C_{30}$) | 0.00 | 0.028 | 0.014 | 0.011 | 0.008 | 1.11 | 1.15 |
| Content of component ($C_X$) in components substituting the component (C) (% by mass) | | ($C_{<5}$)/(C) | 1.10 | 0.10 | 0.10 | 0.10 | 0.10 | 0.00 | 0.00 |
|  |  | ($C_5$)/(C) | 98.90 | 99.90 | 99.90 | 99.90 | 99.90 | 100.00 | 100.00 |
|  |  | ($C_{10}$)/(C) | 93.70 | 99.90 | 99.90 | 99.90 | 99.90 | 100.00 | 100.00 |
|  |  | ($C_{15}$)/C) | 65.60 | 97.50 | 97.50 | 97.50 | 97.50 | 100.00 | 100.00 |
|  |  | ($C_{30}$)/(C) | 0.00 | 2.40 | 2.40 | 2.40 | 2.40 | 96.30 | 100.00 |
| Mass ratio | | (B)/(A) | 2.06 | 2.06 | 2.06 | 2.06 | 2.06 | 2.06 | 2.06 |
|  |  | (C)/(A) | 4.04 | 4.04 | 2.11 | 1.58 | 1.23 | 4.04 | 4.04 |
|  |  | ($C_5$)/(A) | 3.99 | 4.03 | 2.10 | 1.58 | 1.23 | 4.04 | 4.04 |
|  |  | ($C_{10}$)/(A) | 3.78 | 4.03 | 2.10 | 1.58 | 1.23 | 4.04 | 4.04 |
|  |  | ($C_{15}$)/(A) | 2.65 | 3.93 | 2.05 | 1.54 | 1.20 | 4.04 | 4.04 |
|  |  | ($C_{30}$)/(A) | 0.00 | 0.10 | 0.05 | 0.04 | 0.03 | 3.89 | 4.04 |
|  |  | (C)/[(A) + (B)] | 1.32 | 1.32 | 0.69 | 0.52 | 0.40 | 1.32 | 1.32 |
|  |  | ($C_5$)/[(A) + (B)] | 1.30 | 1.32 | 0.69 | 0.51 | 0.40 | 1.32 | 1.32 |
|  |  | ($C_{10}$)/[(A) + (B)] | 1.23 | 1.32 | 0.69 | 0.51 | 0.40 | 1.32 | 1.32 |
|  |  | ($C_{15}$)/[(A) + (B)] | 0.86 | 1.28 | 0.67 | 0.50 | 0.39 | 1.32 | 1.32 |
|  |  | ($C_{30}$)/[(A) + (B)] | 0.00 | 0.03 | 0.02 | 0.01 | 0.01 | 1.27 | 1.32 |
| Evaluation | | Stability evaluation 1 | A | A | B | B | B | A | B |

|  |  | Component name | Example 8 | Example 9 | Example 10 | Comparative Example 1 | Comparative Example 2 | Comparative Example 3 |
|---|---|---|---|---|---|---|---|---|
| Blend (% by mass) | (A) | (A1) 5,6-Dihydroxyindole solution *1 | 25.00 | 25.00 | 25.00 | 25.00 | 25.00 | 25.00 |
|  | (B) | Stearyltrimethylammomum chloride (28%) *2 | 2.10 | 2.10 | 2.10 | 2.10 | 2.10 | 2.10 |
|  | (C) | Polyoxyethylene (15) cetyl ether *3 |  |  |  |  |  |  |
|  |  | Polyoxyethylene (20) cetyl ether *4 | 1.03 |  |  |  | 0.20 |  |
|  |  | Polyoxyethylene (40) cetyl ether *5 |  |  |  |  |  |  |
|  |  | Polyoxyethylene (150) cetyl ether *6 |  |  |  |  |  |  |
|  |  | Polyoxyethylene (10) cetyl ether *7 |  | 4.00 | 8.00 | 1.15 |  |  |
|  |  | Polyoxyethylene (2) cetyl ether *8 | 0.12 |  |  |  |  |  |
|  | Nonionic surfactant | Decyl glucoside (40%) *9 |  |  |  |  |  | 0.55 |
|  | Others | Monoethanolamine *10 | 3.00 | 3.00 | 3.00 | 3.00 | 3.00 | 3.00 |
|  |  | Ascorbic acid *11 | 0.10 | 0.10 | 0.10 | 0.10 | 0.10 | 0.10 |
|  |  | Phosphoric acid (75%) *12 | 1.10 | 1.10 | 1.10 | 1.10 | 1.10 | 1.10 |
|  |  | Water | 67.55 | 64.70 | 60.70 | 67.55 | 68.50 | 68.15 |
|  | Total |  | 100.00 | 100.00 | 100.00 | 100.00 | 100.00 | 100.00 |
| pH |  |  | 10.2 | 10.2 | 10.2 | 10.2 | 10.2 | 10.2 |
| Amount of active component (% by mass) | | Component (A) | 0.29 | 0.29 | 0.29 | 0.29 | 0.29 | 0.29 |
|  |  | Component (B) | 0.59 | 0.59 | 0.59 | 0.59 | 0.59 | 0.59 |
|  |  | Component (C) | 1.15 | 4.00 | 8.00 | 1.15 | 0.20 | 0.00 |
|  |  | Component ($C_5$) | 1.03 | 3.90 | 7.80 | 1.12 | 0.20 | 0.00 |
|  |  | Component ($C_{10}$) | 1.03 | 2.81 | 5.61 | 0.81 | 0.20 | 0.00 |
|  |  | Component ($C_{15}$) | 1.01 | 1.00 | 1.99 | 0.29 | 0.20 | 0.00 |
|  |  | Component ($C_{30}$) | 0.025 | 0.00 | 0.00 | 0.00 | 0.005 | 0.00 |
| Content of component ($C_X$) in components substituting the component (C) | | ($C_{<5}$)/(C) | 10.26 | 2.47 | 2.47 | 2.47 | 0.10 | 0.00 |
|  |  | ($C_5$)/(C) | 89.74 | 97.53 | 97.53 | 97.53 | 99.90 | 0.00 |
|  |  | ($C_{10}$)/(C) | 89.74 | 70.15 | 70.15 | 70.15 | 99.90 | 0.00 |
|  |  | ($C_{15}$)/(C) | 87.58 | 24.90 | 24.90 | 24.90 | 97.50 | 0.00 |

TABLE 1-continued

| (% by mass) | (C$_{30}$)/(C) | 2.16 | 0.00 | 0.00 | 0.00 | 2.40 | 0.00 |
|---|---|---|---|---|---|---|---|
| Mass ratio | (B)/(A) | 2.06 | 2.06 | 2.06 | 2.06 | 2.06 | 2.06 |
| | (C)/(A) | 4.04 | 14.04 | 28.07 | 4.04 | 0.70 | 0.00 |
| | (C$_5$)/(A) | 3.62 | 13.69 | 27.38 | 3.94 | 0.70 | 0.00 |
| | (C$_{10}$)/(A) | 3.62 | 9.85 | 19.69 | 2.83 | 0.70 | 0.00 |
| | (C$_{15}$)/(A) | 3.53 | 3.49 | 6.99 | 1.00 | 0.68 | 0.00 |
| | (C$_{30}$)/(A) | 0.09 | 0.00 | 0.00 | 0.00 | 0.02 | 0.00 |
| | (C)/[(A) + (B)] | 1.32 | 4.58 | 9.16 | 1.32 | 0.23 | 0.00 |
| | (C$_5$)/[(A) + (B)] | 1.18 | 4.47 | 8.94 | 1.28 | 0.23 | 0.00 |
| | (C$_{10}$)/[(A) + (B)] | 1.18 | 3.21 | 6.43 | 0.92 | 0.23 | 0.00 |
| | (C$_{15}$)/[(A) + (B)] | 1.15 | 1.14 | 2.28 | 0.33 | 0.22 | 0.00 |
| | (C$_{30}$)/[(A) + (B)] | 0.03 | 0.00 | 0.00 | 0.00 | 0.01 | 0.00 |
| Evaluation | Stability evaluation 1 | B | B | B | C | C | C |

The components described in Table 1 are shown below. All of the blending amounts (% by mass) described in the table are tangible. In addition, the value expressed as "(C$_X$)/(C)" is the content (% by mass) of the component (C$_X$) in the components constituting the component (C).

*1: (A1) Solution produced by the method described in Japanese Patent No. 5570161 (5,6-dihydroxyindole: 1% by mass, 5,6-dihydroxyindole-2-carboxylic acid: 0.14% by mass, ethanol: 20% by mass, water: remainder)

*2: QUARTAMIN 86W (stearyltrimethylammonium chloride, active component: 28% by mass, manufactured by Kao Corporation)

*3: NIKKOL BC-15 (manufactured by Nikko Chemicals Co., Ltd.)

*4: NIKKOL BC-20 (manufactured by Nikko Chemicals Co., Ltd.)

*5: NIKKOL BC-40TX (manufactured by Nikko Chemicals Co., Ltd.)

*6: NIKKOL BC-150 (manufactured by Nikko Chemicals Co., Ltd.)

*7: NIKKOL BC-10 (manufactured by Nikko Chemicals Co., Ltd.)

*8: NIKKOL BC-2 (manufactured by Nikko Chemicals Co., Ltd.)

*9: MYDOL 10 (manufactured by Kao Corporation)

*10: Monoethanolamine (manufactured by Petronas Chemicals)

*11: Ascorbic acid (Japanese Pharmacopoeia Ascorbic Acid) (manufactured by Watanabe Chemical Co., Ltd.)

*12: Food additive 75% phosphoric acid (manufactured by Nippon Chemical Industrial Co., Ltd.)

TABLE 2

| | | Component name | Example 11 | 12 | 13 | 14 | 15 | 16 |
|---|---|---|---|---|---|---|---|---|
| Blend | (A) | (A1) 5,6-Dihydroxyindole solution *1 | 25.00 | 25.00 | 25.00 | 25.00 | 25.00 | 25.00 |
| (% by mass) | (B) | Lauryltrimethylammonium chloride (27.5%) *13 | 1.61 | | | | | |
| | | Cetyltrimethylammonium chloride (30%) *14 | | 1.79 | | | | |
| | | Stearyltrimethylammonium chloride (28%) *2 | | | 2.09 | | | |
| | | Behenyltrimethylammonium chloride (58%) *15 | | | | 1.17 | | |
| | | Dialkyl(C12-18)dimethylammonium chloride (75%) *16 | | | | | 1.30 | |
| | | Octadecyloxypropyltrimethylammonium chloride *17 | | | | | | 0.72 |
| | (C) | Polyoxyethylene (40) cetyl ether *5 | 3.32 | 3.32 | 3.32 | 3.32 | 3.32 | 3.32 |
| | Others | Monoethanolamine *10 | 3.00 | 3.00 | 3.00 | 3.00 | 3.00 | 3.00 |
| | | Ascorbic acid *11 | 0.10 | 0.10 | 0.10 | 0.10 | 0.10 | 0.10 |
| | | Phosphoric acid (75%) *11 | 1.10 | 1.10 | 1.10 | 1.10 | 1.10 | 1.10 |
| | | Water | 65.87 | 65.69 | 65.39 | 66.31 | 66.18 | 66.76 |
| | | Total | 100.00 | 100.00 | 100.00 | 100.00 | 100.00 | 100.00 |
| pH | | | 10.2 | 10.2 | 10.2 | 10.2 | 10.2 | 10.2 |
| Amount of active component (% by mass) | | Component (A) | 0.29 | 0.29 | 0.29 | 0.29 | 0.29 | 0.29 |
| | | Component (B) | 0.44 | 0.54 | 0.59 | 0.68 | 0.98 | 0.72 |
| | | Component (C) | 3.32 | 3.32 | 3.32 | 3.32 | 3.32 | 3.32 |
| | | Component (C$_5$) | 3.32 | 3.32 | 3.32 | 3.32 | 3.32 | 3.32 |
| | | Component (C$_{10}$) | 3.32 | 3.32 | 3.32 | 3.32 | 3.32 | 3.32 |
| | | Component (C$_{15}$) | 3.32 | 3.32 | 3.32 | 3.32 | 3.32 | 3.32 |
| | | Component (C$_{30}$) | 3.20 | 3.20 | 3.20 | 3.20 | 3.20 | 3.20 |
| Content of component (C$_X$) in components substituting the component (C) (% by mass) | | (C$_{<5}$)/(C) | 0.00 | 0.00 | 0.00 | 0.00 | 0.00 | 0.00 |
| | | (C$_5$)/(C) | 100.00 | 100.00 | 100.00 | 100.00 | 100.00 | 100.00 |
| | | (C$_{10}$)/(C) | 100.00 | 100.00 | 100.00 | 100.00 | 100.00 | 100.00 |
| | | (C$_{15}$)/(C) | 100.00 | 100.00 | 100.00 | 100.00 | 100.00 | 100.00 |
| | | (C$_{30}$)/(C) | 96.30 | 96.30 | 96.30 | 96.30 | 96.30 | 96.30 |
| Mass ratio | | (B)/(A) | 1.55 | 1.88 | 2.05 | 2.38 | 3.42 | 2.53 |
| | | (C)/(A) | 11.65 | 11.65 | 11.65 | 11.65 | 11.65 | 11.65 |
| | | (C$_5$)/(A) | 11.65 | 11.65 | 11.65 | 11.65 | 11.65 | 11.65 |
| | | (C$_{10}$)/(A) | 11.65 | 11.65 | 11.65 | 11.65 | 11.65 | 11.65 |
| | | (C$_{15}$)/(A) | 11.65 | 11.65 | 11.65 | 11.65 | 11.65 | 11.65 |
| | | (C$_{30}$)/(A) | 11.22 | 11.22 | 11.22 | 11.22 | 11.22 | 11.22 |
| | | (C)/[(A) + (B)] | 4.56 | 4.04 | 3.82 | 3.45 | 2.63 | 3.30 |
| | | (C$_5$)/[(A) + (B)] | 4.56 | 4.04 | 3.82 | 3.45 | 2.63 | 3.30 |

TABLE 2-continued

| | | | | | | | |
|---|---|---|---|---|---|---|---|
| | | $(C_{10})/[(A) + (B)]$ | 4.56 | 4.04 | 3.82 | 3.45 | 2.63 | 3.30 |
| | | $(C_{15})/[(A) + (B)]$ | 4.56 | 4.04 | 3.82 | 3.45 | 2.63 | 3.30 |
| | | $(C_{30})/[(A) + (B)]$ | 4.39 | 3.89 | 3.67 | 3.32 | 2.54 | 3.18 |
| Evaluation | | Stability evaluation 1 | A | A | A | B | A | A |

| | | | Comparative Example | | | | | |
|---|---|---|---|---|---|---|---|---|
| | | Component name | 4 | 5 | 6 | 7 | 8 | 9 |
| Blend (% by mass) | (A) | (A1) 5,6-Dihydroxyindole solution *1 | 25.00 | 25.00 | 25.00 | 25.00 | 25.00 | 25.00 |
| | (B) | Lauryltrimethylammonium chloride (27.5%) *13 | 1.61 | | | | | |
| | | Cetyltrimethylammonium chloride (30%) *14 | | 1.79 | | | | |
| | | Stearyltrimethylammonium chloride (28%) *2 | | | 2.09 | | | |
| | | Behenyltrimethylammonium chloride (58%) *15 | | | | 1.17 | | |
| | | Dialkyl(C12-18)dimethylammonium chloride (75%) *16 | | | | | 1.30 | |
| | | Octadecyloxypropyltrimethylammonium chloride *17 | | | | | | 0.72 |
| | (C) | Polyoxyethylene (40) cetyl ether *5 | | | | | | |
| | Others | Monoethanolamine *10 | 3.00 | 3.00 | 3.00 | 3.00 | 3.00 | 3.00 |
| | | Ascorbic acid *11 | 0.10 | 0.10 | 0.10 | 0.10 | 0.10 | 0.10 |
| | | Phosphoric acid (75%) *11 | 1.10 | 1.10 | 1.10 | 1.10 | 1.10 | 1.10 |
| | | Water | 69.19 | 69.01 | 68.71 | 69.63 | 69.50 | 70.08 |
| | Total | | 100.00 | 100.00 | 100.00 | 100.00 | 100.00 | 100.00 |
| pH | | | 10.2 | 10.2 | 10.2 | 10.2 | 10.2 | 10.2 |
| Amount of active component (% by mass) | | Component (A) | 0.29 | 0.29 | 0.29 | 0.29 | 0.29 | 0.29 |
| | | Component (B) | 0.44 | 0.54 | 0.59 | 0.68 | 0.98 | 0.72 |
| | | Component (C) | 0.00 | 0.00 | 0.00 | 0.00 | 0.00 | 0.00 |
| | | Component $(C_5)$ | 0.00 | 0.00 | 0.00 | 0.00 | 0.00 | 0.00 |
| | | Component $(C_{10})$ | 0.00 | 0.00 | 0.00 | 0.00 | 0.00 | 0.00 |
| | | Component $(C_{15})$ | 0.00 | 0.00 | 0.00 | 0.00 | 0.00 | 0.00 |
| | | Component $(C_{30})$ | 0.00 | 0.00 | 0.00 | 0.00 | 0.00 | 0.00 |
| Content of component $(C_X)$ in components substituting the component (C) (% by mass) | | $(C_{<5})/(C)$ | 0.00 | 0.00 | 0.00 | 0.00 | 0.00 | 0.00 |
| | | $(C_5)/(C)$ | 0.00 | 0.00 | 0.00 | 0.00 | 0.00 | 0.00 |
| | | $(C_{10})/(C)$ | 0.00 | 0.00 | 0.00 | 0.00 | 0.00 | 0.00 |
| | | $(C_{15})/(C)$ | 0.00 | 0.00 | 0.00 | 0.00 | 0.00 | 0.00 |
| | | $(C_{30})/(C)$ | 0.00 | 0.00 | 0.00 | 0.00 | 0.00 | 0.00 |
| Mass ratio | | (B)/(A) | 1.55 | 1.88 | 2.05 | 2.38 | 3.42 | 2.53 |
| | | (C)/(A) | 0.00 | 0.00 | 0.00 | 0.00 | 0.00 | 0.00 |
| | | $(C_5)/(A)$ | 0.00 | 0.00 | 0.00 | 0.00 | 0.00 | 0.00 |
| | | $(C_{10})/(A)$ | 0.00 | 0.00 | 0.00 | 0.00 | 0.00 | 0.00 |
| | | $(C_{15})/(A)$ | 0.00 | 0.00 | 0.00 | 0.00 | 0.00 | 0.00 |
| | | $(C_{30})/(A)$ | 0.00 | 0.00 | 0.00 | 0.00 | 0.00 | 0.00 |
| | | $(C)/[(A) + (B)]$ | 0.00 | 0.00 | 0.00 | 0.00 | 0.00 | 0.00 |
| | | $(C_5)/[(A) + (B)]$ | 0.00 | 0.00 | 0.00 | 0.00 | 0.00 | 0.00 |
| | | $(C_{10})/[(A) + (B)]$ | 0.00 | 0.00 | 0.00 | 0.00 | 0.00 | 0.00 |
| | | $(C_{15})/[(A) + (B)]$ | 0.00 | 0.00 | 0.00 | 0.00 | 0.00 | 0.00 |
| | | $(C_{30})/[(A) + (B)]$ | 0.00 | 0.00 | 0.00 | 0.00 | 0.00 | 0.00 |
| Evaluation | | Stability evaluation 1 | C | C | C | C | C | C |

The components described in Table 2 are shown below. All of the blending amounts (% by mass) described in the table are tangible. In addition, the value expressed as "$(C_X)/(C)$" is the content (% by mass) of the component $(C_X)$ in the components constituting the component (C).

*1: (A1) Solution produced by the method described in Japanese Patent No. 5570161 (5,6-dihydroxyindole: 1% by mass, 5,6-dihydroxyindole-2-carboxylic acid: 0.14% by mass, ethanol: 20% by mass, water: remainder)

*2: QUARTAMIN 86W (stearyltrimethylammonium chloride, active component: 28% by mass, manufactured by Kao Corporation)

*5: NIKKOL BC-40TX (manufactured by Nikko Chemicals Co., Ltd.)

*10: Monoethanolamine (manufactured by Petronas Chemicals)

*11: Ascorbic acid (Japanese Pharmacopoeia Ascorbic Acid) (manufactured by Watanabe Chemical Co., Ltd.)

*12: Food additive 75% phosphoric acid (manufactured by Nippon Chemical Industrial Co., Ltd.)

*13: QUARTAMIN 24P (lauryltrimethylammonium chloride, active component: 27.5% by mass, manufactured by Kao Corporation)

*14: QUARTAMIN 60W (cetyltrimethylammonium chloride, active component: 30% by mass, manufactured by Kao Corporation)

*15: QUARTAMIN 2285E (behenyltrimethylammonium chloride, active component: 58% by mass, manufactured by Kao Corporation)

*16: QUARTAMIN D-2345P (dialkyl($C_{12-18}$)dimethylammonium chloride, active component: 75% by mass, manufactured by Kao Corporation)

*17: QUARTAMIN E-80K (octadecyloxypropyltrimethylammonium chloride, active component: 100% by mass, manufactured by Kao Corporation)

The following are noted from Tables 1 and 2.

In the hair cosmetics of Examples 1 to 16, an aggregate owing to the component (A) and the component (B) is not produced even in an alkaline region, and excellent stability is obtained.

From comparison of Examples 1 to 10 with Comparative Examples 1 to 3 in Table 1, in the case where any of the expressions (I) to (IV) are not satisfied, an aggregate owing to the component (A) and the component (B) is produced, and the stability is lowered.

In addition, from comparison of Examples 11 to 16 with Comparative Examples 4 to 9 in Table 2, when at least one of the expressions (I) to (IV) is satisfied, favorable stability can be obtained regardless of the kind of the cationic surfactant of the component (B) to be used for the hair cosmetic, and in the case where the component (C) is not contained, the stability is lowered.

Examples 17 to 31 and Comparative Examples 10 to 11

[Preparation of Hair Cosmetic (Hair Treatment Agent)]

The component (B), an alkaline agent, phosphoric acid, and a part of water were mixed to prepare aqueous solutions according to formulations shown in Tables 3 and 4, followed by keeping at 75° C. Thereafter, a mixture of other components than the component (A), ascorbic acid, and sodium sulfite was added. The resulting mixture was gradually cooled and controlled to a temperature of 30° C. Then, ascorbic acid, sodium sulfite, and a solution of the component (A) were added in a nitrogen atmosphere, to prepare hair cosmetics. All of the hair cosmetics had a pH of 10.2.

The prepared hair cosmetics were stored in a nitrogen atmosphere and dispersed on each occasion of evaluation, and the following evaluations were carried out.

[Stability Evaluation 2 of Hair Cosmetic]

The stability evaluation 2 of the hair cosmetic was performed by aliquoting and spreading 0.1 g of the hair cosmetic prepared by the aforementioned method on a slide glass and then placing a cover glass thereon at 25° C., followed by confirming the presence or absence of any deposit in the hair cosmetic through visual observation and microscopic observation. The evaluation criteria are as follows.

A: A deposit is not perceived at all.

B: A state where a deposit is perceived but minute, and is uniformly dispersed.

C: A state where a deposit is perceived and aggregated, and it locally exists as a whole.

[Touch Evaluation during Rinsing of Hair]

For the touch evaluation, a black hair tress having a length of 30 cm and a mass of 10 g (BS-B3A, manufactured by Beaulax Co., Ltd.) was used.

The aforementioned black hair tress was cleansed once with a plain shampoo having a composition shown below and then air-dried. The resultant was further subjected to a bleach treatment once for 30 minutes, cleansed once with the plain shampoo, and then air-dried. This tress was subjected to the following touch evaluation.

| (Plain Shampoo) | (% by mass) |
|---|---|
| Sodium polyoxyethylene lauryl ether sulfate: (EMAL E-27C (active component amount: 27% by mass), manufactured by Kao Corporation) | 57.4 |
| Lauramide DEA: (AMINON L-02, manufactured by Kao Corporation | 1.5 |
| EDTA-2Na: (FROST DS, manufactured by Daiichi Pure Chemical Co., Ltd.) | 0.3 |
| Phosphoric acid (adjusted at a pH of 7.0) | Moderate |
| Purified water | Remainder |
| Total | 100 |

The tress for evaluation which had been rinsed with warm water for 30 seconds in advance was shampooed with the aforementioned plain shampoo for 15 seconds and then rinsed with warm water for 30 seconds. 4 g of the hair cosmetic obtained in each of the Examples was uniformly applied on this tress in a bath ratio of 1/0.5/0.5 (tress/water/hair cosmetic) and then allowed to stand in an atmosphere at 30° C. for 5 minutes. Subsequently, the applied hair cosmetic was rinsed with warm water for 30 seconds.

In the touch evaluation, with respect to the touch during rinsing of the hair cosmetic, six expert panelists evaluated at the time of combing fingers through the tress from the root of the hair toward the hair end direction. The evaluation value was determined in terms of a number of panelists who evaluated "smooth and favorable touch without being caught".

TABLE 3

| | | | Example | | | | | | |
|---|---|---|---|---|---|---|---|---|---|
| | | Component name | 17 | 18 | 19 | 20 | 21 | 22 | 23 |
| Blend (% by mass) | (A) | (A1) 5.6-Dihydroxyindole solution *[1] | 5.00 | 7.50 | 15.00 | 25.00 | 25.00 | 25.00 | 25.00 |
| | | (A2) 5,6-Dihydroxyindole solution *[18] | | | | | | | |
| | | (A3) 5,6-Dihydroxyindoline•HBr solution *[19] | | | | | | | |
| | (B) | Stearyltrimethylammonium chloride (28%) *[2] | 3.11 | 3.11 | 3.11 | 3.11 | 1.61 | 1.11 | 3.14 |
| | (C) | Polyoxyethylene (40) cetyl ether *[5] | 0.95 | 0.95 | 0.95 | 0.95 | 0.95 | 0.95 | 0.49 |
| | | Polyoxyethylene (2) cetyl ether *[8] | 0.45 | 0.45 | 0.45 | 0.45 | 0.45 | 0.45 | 0.23 |
| | Others | Monoethanolamine *[10] | 3.00 | 3.00 | 3.00 | 3.00 | 3.00 | 3.00 | 3.00 |
| | | Stearyl alcohol *[20] | 2.10 | 2.10 | 2.10 | 2.10 | 2.10 | 2.10 | 2.10 |
| | | Behenyl alcohol *[21] | 4.10 | 4.10 | 4.10 | 4.10 | 4.10 | 4.10 | 4.10 |
| | | Oleyl alcohol *[22] | | | | | | | |
| | | Liquid paraffin *[23] | 3.80 | 3.80 | 3.80 | 3.80 | 3.80 | 3.80 | 3.80 |
| | | Sodium sulfite *[24] | 0.50 | 0.50 | 0.50 | 0.50 | 0.50 | 0.50 | 0.50 |
| | | Ascorbic acid *[11] | 0.60 | 0.60 | 0.60 | 0.60 | 0.60 | 0.60 | 0.60 |
| | | Phosphoric acid (75%) *[12] | 0.48 | 0.48 | 0.48 | 0.48 | 0.48 | 0.48 | 0.48 |
| | | Oxidation dye X *[2B] | | | | | | | |
| | | Oxidation dye Y *[26] | | | | | | | |
| | | Propylene glycol *[27] | 1.00 | 1.00 | 1.00 | 1.00 | 1.00 | 1.00 | 2.00 |
| | | Water | 74.91 | 72.41 | 64.91 | 54.91 | 56.41 | 56.91 | 54.56 |
| | Total | | 100.00 | 100.00 | 100.00 | 100.00 | 100.00 | 100.00 | 100.00 |
| pH | | | 10.2 | 10.2 | 10.2 | 10.2 | 10.2 | 10.2 | 10.2 |
| Amount of active component (% by mass) | | Component (A) | 0.06 | 0.09 | 0.17 | 0.29 | 0.29 | 0.29 | 0.29 |
| | | Component (B) | 0.87 | 0.87 | 0.87 | 0.87 | 0.45 | 0.31 | 0.88 |
| | | Component (C) | 1.40 | 1.40 | 1.40 | 1.40 | 1.40 | 1.40 | 0.72 |
| | | Component ($C_5$) | 1.02 | 1.02 | 1.02 | 1.02 | 1.02 | 1.02 | 0.53 |
| | | Component ($C_{10}$) | 0.95 | 0.95 | 0.95 | 0.95 | 0.95 | 0.95 | 0.49 |

TABLE 3-continued

|  |  |  |  |  |  |  |  |  |
|---|---|---|---|---|---|---|---|---|
| Content of oily components (% by mass) | Component ($C_{15}$) | 0.95 | 0.95 | 0.95 | 0.95 | 0.95 | 0.95 | 0.49 |
|  | Component ($C_{30}$) | 0.91 | 0.91 | 0.91 | 0.91 | 0.91 | 0.91 | 0.47 |
|  | Higher alcohol | 6.20 | 6.20 | 6.20 | 6.20 | 6.20 | 6.20 | 6.20 |
|  | Oil | 3.80 | 3.80 | 3.80 | 3.80 | 3.80 | 3.80 | 3.80 |
|  | Total of oily components | 10.00 | 10.00 | 10.00 | 10.00 | 10.00 | 10.00 | 10.00 |
| Content of component ($C_X$) in components substituting the component (C) (% by mass) | ($C_{<5}$)/(C) | 27.22 | 27.22 | 27.22 | 27.22 | 27.22 | 27.22 | 27.05 |
|  | ($C_5$)/(C) | 72.78 | 72.78 | 72.78 | 72.78 | 72.78 | 72.78 | 72.95 |
|  | ($C_{10}$)/(C) | 68.06 | 68.06 | 68.06 | 68.06 | 68.06 | 68.06 | 68.26 |
|  | ($C_{15}$)/(C) | 67.86 | 67.86 | 67.86 | 67.86 | 67.86 | 67.86 | 68.06 |
|  | ($C_{30}$)/(C) | 65.35 | 65.35 | 65.35 | 65.35 | 65.35 | 65.35 | 65.54 |
| Mass ratio | (B)/(A) | 15.28 | 10.18 | 5.09 | 3.05 | 1.58 | 1.09 | 3.08 |
|  | (C)/(A) | 24.56 | 16.37 | 8.19 | 4.91 | 4.91 | 4.91 | 2.53 |
|  | ($C_5$)/(A) | 17.88 | 11.92 | 5.96 | 3.58 | 3.58 | 3.58 | 1.84 |
|  | ($C_{10}$)/(A) | 16.72 | 11.14 | 5.57 | 3.34 | 3.34 | 3.34 | 1.72 |
|  | ($C_{15}$)/(A) | 16.67 | 11.11 | 5.56 | 3.33 | 3.33 | 3.33 | 1.72 |
|  | ($C_{30}$)/(A) | 16.05 | 10.70 | 5.35 | 3.21 | 3.21 | 3.21 | 1.66 |
|  | (C)/[(A) + (B)] | 1.51 | 1.47 | 1.34 | 1.21 | 1.90 | 2.35 | 0.62 |
|  | ($C_5$)/[(A) + (B)] | 1.10 | 1.07 | 0.98 | 0.88 | 1.38 | 1.71 | 0.45 |
|  | ($C_{10}$)/[(A) + (B)] | 1.03 | 1.00 | 0.92 | 0.83 | 1.30 | 1.60 | 0.42 |
|  | ($C_{15}$)/[(A) + (B)] | 1.02 | 0.99 | 0.91 | 0.82 | 1.29 | 1.59 | 0.42 |
|  | ($C_{30}$)/[(A) + (B)] | 0.99 | 0.96 | 0.88 | 0.79 | 1.24 | 1.54 | 0.41 |
| Evaluation | Stability evaluation 2 | A | A | A | A | A | A | A |
|  | Touch during rinsing of hair | 6 | 6 | 6 | 5 | 4 | 3 | 6 |

|  |  | Example |  |  |  |  | Comparative Example |  |
|---|---|---|---|---|---|---|---|---|
|  | Component name | 24 | 25 | 26 | 27 | 28 | 10 | 11 |
| Blend (% by mass) | (A) (A1) 5,6-Dihydroxyindole solution *[1] | 25.00 |  |  | 25.00 | 25.00 | 25.00 | 25.00 |
|  | (A2) 5,6-Dihydroxyindole solution *[18] |  | 25.00 |  |  |  |  |  |
|  | (A3) 5,6-Dihydroxyindoline·HBr solution *[19] |  |  | 25.00 |  |  |  |  |
|  | (B) Stearyltrimethylammonium chloride (28%) *[2] | 3.11 | 3.14 | 3.14 | 3.14 | 3.14 | 0.79 | 3.11 |
|  | (C) Polyoxyethylene (40) cetyl ether *[5] | 0.35 | 1.09 | 1.09 | 1.09 | 1.09 | 0.95 | 0.17 |
|  | Polyoxyethylene (2) cetyl ether *[8] | 0.16 | 0.48 | 0.48 | 0.48 | 0.48 | 0.45 | 0.08 |
|  | Others Monoethanolamine *[10] | 3.00 | 3.00 | 3.00 | 3.00 | 3.00 | 3.00 | 3.00 |
|  | Stearyl alcohol *[20] | 2.10 | 2.20 | 2.20 | 2.20 | 2.20 | 2.10 | 2.10 |
|  | Behenyl alcohol *[21] | 4.10 | 2.78 | 2.78 | 2.78 | 2.78 | 4.10 | 4.10 |
|  | Oleyl alcohol *[22] |  | 0.85 | 0.85 | 0.85 | 0.85 |  |  |
|  | Liquid paraffin *[23] | 3.80 | 1.70 | 1.70 | 1.70 | 1.70 | 3.80 | 3.80 |
|  | Sodium sulfite *[24] | 0.50 | 0.50 | 0.50 | 0.50 | 0.50 | 0.50 | 0.50 |
|  | Ascorbic acid *[11] | 0.60 | 0.60 | 0.60 | 0.60 | 0.60 | 0.60 | 0.60 |
|  | Phosphoric acid (75%) *[12] | 0.48 | 0.48 | 0.48 | 0.48 | 0.48 | 0.48 | 0.48 |
|  | Oxidation dye X *[2B] |  |  |  | 0.035 |  |  |  |
|  | Oxidation dye Y *[26] |  |  |  |  | 0.035 |  |  |
|  | Propylene glycol *[27] | 1.00 | 2.00 | 2.00 | 2.00 | 2.00 | 1.00 | 2.00 |
|  | Water | 55.80 | 56.18 | 56.18 | 56.15 | 56.15 | 57.23 | 55.06 |
| Total |  | 100.00 | 100.00 | 100.00 | 100.00 | 100.00 | 100.00 | 100.00 |
| pH |  | 10.2 | 10.2 | 10.2 | 10.2 | 10.2 | 10.2 | 10.2 |
| Amount of active component (% by mass) | Component (A) | 0.29 | 0.25 | 0.25 | 0.29 | 0.29 | 0.29 | 0.29 |
|  | Component (B) | 0.87 | 0.88 | 0.88 | 0.88 | 0.88 | 0.22 | 0.87 |
|  | Component (C) | 0.51 | 1.57 | 1.57 | 1.57 | 1.57 | 1.40 | 0.25 |
|  | Component ($C_5$) | 0.38 | 1.16 | 1.16 | 1.16 | 1.16 | 1.02 | 0.18 |
|  | Component ($C_{10}$) | 0.35 | 1.09 | 1.09 | 1.09 | 1.09 | 0.95 | 0.17 |
|  | Component ($C_{15}$) | 0.35 | 1.09 | 1.09 | 1.09 | 1.09 | 0.95 | 0.17 |
|  | Component ($C_{30}$) | 0.34 | 1.05 | 1.05 | 1.05 | 1.05 | 0.91 | 0.16 |
| Content of oily components (% by mass) | Higher alcohol | 6.20 | 5.83 | 5.83 | 5.83 | 5.83 | 6.20 | 6.20 |
|  | Oil | 3.80 | 1.70 | 1.70 | 1.70 | 1.70 | 3.80 | 3.80 |
|  | Total of oily components | 10.00 | 7.53 | 7.53 | 7.53 | 7.53 | 10.00 | 10.00 |
| Content of component ($C_X$) in components substituting the component (C) (% by mass) | ($C_{<5}$)/(C) | 27.09 | 25.89 | 25.89 | 25.89 | 25.89 | 27.22 | 27.09 |
|  | ($C_5$)/(C) | 72.91 | 74.11 | 74.11 | 74.11 | 74.11 | 72.78 | 72.91 |
|  | ($C_{10}$)/(C) | 68.20 | 69.62 | 69.62 | 69.62 | 69.62 | 68.06 | 68.20 |
|  | ($C_{15}$)/(C) | 68.00 | 69.43 | 69.43 | 69.43 | 69.43 | 67.86 | 68.00 |
|  | ($C_{30}$)/(C) | 65.48 | 66.86 | 66.86 | 66.86 | 66.86 | 65.35 | 65.48 |
| Mass ratio | (B)/(A) | 3.06 | 3.52 | 3.52 | 3.08 | 3.08 | 0.78 | 3.06 |
|  | (C)/(A) | 1.81 | 6.28 | 6.28 | 5.51 | 5.51 | 4.91 | 0.88 |
|  | ($C_5$)/(A) | 1.32 | 4.65 | 4.65 | 4.08 | 4.08 | 3.58 | 0.64 |
|  | ($C_{10}$)/(A) | 1.23 | 4.37 | 4.37 | 3.84 | 3.84 | 3.34 | 0.60 |
|  | ($C_{15}$)/(A) | 1.23 | 4.36 | 4.36 | 3.82 | 3.82 | 3.33 | 0.60 |
|  | ($C_{30}$)/(A) | 1.18 | 4.20 | 4.20 | 3.68 | 3.68 | 3.21 | 0.57 |
|  | (C)/[(A) + (B)] | 0.45 | 1.39 | 1.39 | 1.35 | 1.35 | 2.77 | 0.22 |
|  | ($C_5$)/[(A) + (B)] | 0.32 | 1.03 | 1.03 | 1.00 | 1.00 | 2.01 | 0.16 |

TABLE 3-continued

|  |  |  |  |  |  |  |  |  |
|---|---|---|---|---|---|---|---|---|
|  | ($C_{10}$)/[(A) + (B)] | 0.30 | 0.97 | 0.97 | 0.94 | 0.94 | 1.88 | 0.15 |
|  | ($C_{15}$)/[(A) + (B)] | 0.30 | 0.97 | 0.97 | 0.94 | 0.94 | 1.88 | 0.15 |
|  | ($C_{30}$)/[(A) + (B)] | 0.29 | 0.93 | 0.93 | 0.90 | 0.90 | 1.81 | 0.14 |
| Evaluation | Stability evaluation 2 | B | A | A | A | A | A | C |
|  | Touch during rinsing of hair | 4 | 6 | 6 | 6 | 6 | 2 | 4 |

TABLE 4

|  |  |  | Example | | |
|---|---|---|---|---|---|
|  |  | Component name | 29 | 30 | 31 |
| Blend | (A) | (A1) 5,6-Dihydroxyindole solution *[1] | 25.00 | 25.00 | 25.00 |
| (% by mass) | (B) | Stearyltrimethylammonium chloride (28%) *[2] | 2.11 | 2.11 | 2.11 |
|  | (C) | Polyoxyethylene (40) cetyl ether *[5] | 2.66 | 3.53 | 5.33 |
|  |  | Polyoxyethylene (2) cetyl ether *[8] | 0.55 | 0.37 | 0.00 |
|  | Others | Monoethanolamine *[10] | 3.00 | 3.00 | 3.00 |
|  |  | Stearyl alcohol *[20] | 4.66 | 4.66 | 4.66 |
|  |  | Behenyl alcohol *[21] | 1.34 | 1.34 | 1.34 |
|  |  | Oleyl alcohol *[22] | 0.85 | 0.85 | 0.85 |
|  |  | Liquid paraffin *[25] | 1.70 | 1.70 | 1.70 |
|  |  | Sodium sulfite *[24] | 0.50 | 0.50 | 0.50 |
|  |  | Ascorbic acid *[11] | 0.60 | 0.60 | 0.60 |
|  |  | Phosphoric acid (75%) *[12] | 0.48 | 0.48 | 0.48 |
|  |  | Propylene glycol *[27] | 2.00 | 2.00 | 2.00 |
|  |  | Water | 54.55 | 53.86 | 52.43 |
|  | Total |  | 100.00 | 100.00 | 100.00 |
| pH |  |  | 10.2 | 10.2 | 10.2 |
| Amount of active |  | Component (A) | 0.29 | 0.29 | 0.29 |
| component |  | Component (B) | 0.59 | 0.59 | 0.59 |
| (% by mass) |  | Component (C) | 3.21 | 3.90 | 5.33 |
|  |  | Component ($C_5$) | 2.74 | 3.59 | 5.33 |
|  |  | Component ($C_{10}$) | 2.66 | 3.53 | 5.33 |
|  |  | Component ($C_{15}$) | 2.66 | 3.53 | 5.33 |
|  |  | Component ($C_{30}$) | 2.56 | 3.40 | 5.13 |
| Content of oily |  | Higher alcohol | 6.85 | 6.85 | 6.85 |
| components (% by mass) |  | Oil | 1.70 | 1.70 | 1.70 |
|  |  | Total of oily components | 8.55 | 8.55 | 8.55 |
| Content of |  | ($C_{<5}$)/(C) | 14.51 | 8.03 | 0.00 |
| component ($C_X$) in |  | ($C_5$)/(C) | 85.49 | 91.97 | 100.00 |
| components substituting |  | ($C_{10}$)/(C) | 82.98 | 90.57 | 100.00 |
| the component (C) |  | ($C_{15}$)/(C) | 82.87 | 90.51 | 100.00 |
| (% by mass) |  | ($C_{30}$)/(C) | 79.80 | 87.16 | 96.30 |
| Mass ratio |  | (B)/(A) | 2.07 | 2.07 | 2.07 |
|  |  | (C)/(A) | 11.26 | 13.68 | 18.70 |
|  |  | ($C_5$)/(A) | 9.63 | 12.58 | 18.70 |
|  |  | ($C_{10}$)/(A) | 9.35 | 12.39 | 18.70 |
|  |  | ($C_{15}$)/(A) | 9.33 | 12.39 | 18.70 |
|  |  | ($C_{30}$)/(A) | 8.99 | 11.93 | 18.01 |
|  |  | (C)/[(A) + (B)] | 3.67 | 4.45 | 6.09 |
|  |  | ($C_5$)/[(A) + (B)] | 3.13 | 4.10 | 6.09 |
|  |  | ($C_{10}$)/[(A) + (B)] | 3.04 | 4.03 | 6.09 |
|  |  | ($C_{15}$)/[(A) + (B)] | 3.04 | 4.03 | 6.09 |
|  |  | ($C_{30}$)/[(A) + (B)] | 2.92 | 3.88 | 5.86 |
| Evaluation |  | Stability evaluation 2 | A | A | A |
|  |  | Touch during rinsing of hair | 4 | 3 | 3 |

The components described in Tables 3 and 4 are shown below. All of the blending amounts (% by mass) described in the table are tangible. In addition, the value expressed as "($C_X$)/(C)" is the content (% by mass) of the component ($C_X$) in the components constituting the component (C).

*1: (A1) Solution produced by the method described in Japanese Patent No. 5570161 (5,6-dihydroxyindole: 1% by mass, 5,6-dihydroxyindole-2-carboxylic acid: 0.14% by mass, ethanol: 20% by mass, water: remainder)

*2: QUARTAMIN 86W (stearyltrimethylammonium chloride, active component: 28% by mass, manufactured by Kao Corporation)

*5: NIKKOL BC-40TX (manufactured by Nikko Chemicals Co., Ltd.)

*8: NIKKOL BC-2 (manufactured by Nikko Chemicals Co., Ltd.)

*10: Monoethanolamine (manufactured by Petronas Chemicals)

*11: Ascorbic acid (Japanese Pharmacopoeia Ascorbic Acid) (manufactured by Watanabe Chemical Co., Ltd.)

*12: Food additive 75% phosphoric acid (manufactured by Nippon Chemical Industrial Co., Ltd.)

*18: (A2) 5,6-Dihydroxyindole solution (manufactured by Matrix Scientific, 5,6-dihydroxyindole: 1% by mass, ethanol: 20% by mass, water: remainder)

*19: (A3) 5,6-Dihydroxyindoline hydrobromide solution (manufactured by AK-scientific, 5,6-dihydroxyindoline hydrobromide: 1% by mass, ethanol: 20% by mass, water: remainder)
*20: KALCOL 8098 (manufactured by Kao Corporation)
*21: KALCOL 220-80 (manufactured by Kao Corporation)
*22: OLEYL #1500S (manufactured by Nippon Suisan Kaisha, Ltd.)
*23: HICALL K-350 (manufactured by Kaneda Co., Ltd.)
*24: Purified anhydrous sodium sulfite (manufactured by Daito Chemical Co., Ltd.)
*25: Oxidation dye X: Toluene-2,5-diamine sulfate, paraaminophenol, metaaminophenol, resorcin, 2,4-diaminophenoxyethanol hydrochloride, 5-aminoorthocresol, and paraphenylenediamine sulfate, each of which is blended in an amount of 0.005% by mass in the hair cosmetic
*26: Oxidation dye Y: 2-Methylresorcin, 4-aminometacresol, 2-amino-3-hydroxypyridine, 2-amino-4-(6-hydroxyethyl)aminoanisole sulfate, 4-chlororesorcinol, 1-naphthol, and 1-hydroxyethyl-4,5-diaminopyrazole sulfate, each of which is blended in an amount of 0.005% by mass in the hair cosmetic
*27: Propylene glycol for cosmetic (manufactured by ADEKA CORPORATION)

From Tables 3 and 4, it is noted that the hair cosmetics of Examples 17 to 31 are favorable in all of stability and touch during rinsing of hair. On the other hand, in the hair cosmetic of Comparative Example 10, since the mass ratio (B)/(A) of the component (B) to the component (A) is less than 1.0, the touch during rinsing of hair is lowered. In addition, in the hair cosmetic of Comparative Example 11, since the mass ratio (C)/(A) of the component (C) to the component (A) is less than 1.0, the stability is lowered.

INDUSTRIAL APPLICABILITY

The hair cosmetic of the present invention hardly produces an aggregate to be caused owing to complex formation between a predetermined melanin precursor and a cationic surfactant even in an alkaline region and is excellent in stability and favorable in touch of the hair during rinsing. In addition, when the hair cosmetic of the present invention is used, it is able to readily perform dyeing of gray hair and the like through a daily hair care behavior.

The invention claimed is:
1. A hair cosmetic, comprising:
(A) a compound represented by the following formula (1) or a salt thereof:

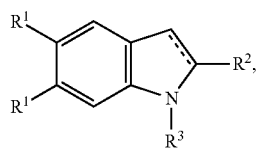

wherein a broken line represents the presence or absence of a π bond; $R^1$ represents a hydroxy group or an acetoxy group; $R^2$ represents a hydrogen atom or —COOR, wherein R is a hydrogen atom, a methyl group, or an ethyl group; and $R^3$ represents a hydrogen atom, an acetyl group, a methyl group, or an ethyl group;

(B) a cationic surfactant, wherein the cationic surfactant is a mono- or di-long chain alkyl quaternary ammonium salt represented by the following formula:

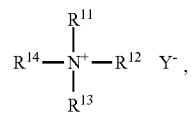

wherein $R^{11}$ is a linear or branched alkyl group having from 8 to 18 carbon atoms or a group represented by $R^{15}CONH(CH_2)_m—$, $R^{15}—O—(CH_2)_m—$, or $R^{15}COO(CH_2)_m—$, wherein $R^{15}$ represents a linear or branched alkyl group having from 7 to 21 carbon atoms, and m represents a number of from 1 to 4; $R^{12}$ represents a linear or branched alkyl group having from 1 to 22 carbon atoms or a group represented by the foregoing $R^{15}CONH(CH_2)_m—$, $R^{15}—O—(CH_2)_m—$, or $R^{15}COO(CH_2)_m—$; $R^{13}$ and $R^{14}$ each independently represent an alkyl group from 1 to 4 carbon atoms; and $Y^-$ represents a chloride ion, a bromide ion, or a methosulfate ion; and
(C) a polyoxyethylene addition nonionic surfactant having an oxyethylene addition molar number of 100 or less,
wherein:
a mass ratio of the component (B) to the component (A), [(B)/(A)], is at least 1.0, and a mass ratio of the component (C) to the component (A), [(C)/(A)], is at least 2.5;
when in components constituting the component (C), a component having an oxyethylene addition molar number of 5 or more is designated as $(C_5)$, a component having an oxyethylene addition molar number of 10 or more is designated as $(C_{10})$, a component having an oxyethylene addition molar number of 15 or more is designated as $(C_{15})$, and a component having an oxyethylene addition molar number of 30 or more is designated as $(C_{30})$, a mass ratio of each of the components relative to the component (A) satisfies at least one of the following expressions (I) to (IV):

$$(C_5)/(A) \geq 4.5 \quad (I),$$

$$(C_{10})/(A) \geq 3.5 \quad (II),$$

$$(C_{15})/(A) \geq 1.2 \quad (III),$$

$$(C_{30})/(A) \geq 0.2 \quad (IV);\text{ and}$$

a pH at 25° C. of the hair cosmetic is from 8.0 to 12.0,
wherein, when the hair cosmetic further comprises a higher alcohol and a content of the higher alcohol in the hair cosmetic is less than 3% by mass, a component having an oxyethylene addition molar number of less than 5 in the components constituting the component (C) is designated as $(C_{<5})$, and a content of the component $(C_{<5})$ in the components constituting the component (C) is 5% by mass or less, and
wherein the hair cosmetic satisfies at least one of the following (VII) to (VIII);
(VII) a content of the component $(C_{15})$ in the components constituting the component (C) is at least 30% by mass, and
(VIII) a content of the component $(C_{30})$ in the components constituting the component (C) is more than 0% by mass.

2. The hair cosmetic according to claim 1, wherein components constituting the component (C) further comprise a component having an oxyethylene addition molar number of 200 or more which is designated as ($C_{200}$), and a mass ratio ($C_{200}$)/(A) of the component ($C_{200}$) to the component (A) is 5.0 or less.

3. The hair cosmetic according to claim 1, wherein the mass ratio (B)(A) of the component (B) to the component (A) is from 1.5 to 20.

4. The hair cosmetic according to claim 1, wherein the mass ratio (C)/(A) of the component (C) to the component (A) is from 2.5 to 25.

5. The hair cosmetic according to claim 1, wherein the component (C) is a polyoxyethylene alkyl ether.

6. The hair cosmetic according to claim 5, wherein the polyoxyethylene alkyl ether comprises at least one selected from the group consisting of polyoxyethylene lauryl ether, polyoxyethylene myristyl ether, polyoxyethylene cetyl ether, polyoxyethylene stearyl ether, and polyoxyethylene behenyl ether.

7. The hair cosmetic according to claim 1, which further satisfies at least one of the following (V) and (VI):
(V) a content of the component ($C_5$) in the components constituting the component (C) is at least 98% by mass, and
(VI) a content of the component ($C_{10}$) in the components constituting the component (C) is at least 75% by mass.

8. The hair cosmetic according to claim 1, wherein a content of the component (A) in the hair cosmetic is from 0.05% by mass to 5% by mass.

9. The hair cosmetic according to claim 1, wherein the components constituting the component (C) further comprise a component having an oxyethylene addition molar number of 70 or more designated as ($C_{70}$), and a mass ratio ($C_{70}$)/(A) of the component ($C_{70}$) to the component (A) is 5.0 or less.

10. The hair cosmetic according to claim 1, wherein the pH at 25° C. of the hair cosmetic is from 9.0 to 11.0.

11. A method of dyeing hair, comprising:
applying the hair cosmetic according to claim 1 on hair.

12. The hair cosmetic according to claim 1, wherein $R^{11}$ is the linear or branched alkyl group having from 8 to 18 carbon atoms.

13. The hair cosmetic of claim 1, further comprising the higher alcohol.

14. The hair cosmetic of claim 13, wherein the higher alcohol is at least one selected form the group consisting of a lauryl alcohol, myristyl alcohol, cetyl alcohol, stearyl alcohol, isostearyl alcohol, arachidyl alcohol, behenyl alcohol, carnaubyl alcohol, and oleyl alcohol.

* * * * *